United States Patent [19]
Pfrengle et al.

[11] Patent Number: 6,020,338
[45] Date of Patent: Feb. 1, 2000

[54] FUNGICIDAL 7-ALKYL-TRIAZOLOPYRIMIDINES

[75] Inventors: Waldemar Pfrengle, Seibersbach; Klaus-Juergen Pees, Mainz; Guido Albert, Hackenheim, all of Germany

[73] Assignee: American Cyanamid Company, Madison, N.J.

[21] Appl. No.: 09/243,851

[22] Filed: Feb. 3, 1999

Related U.S. Application Data

[60] Provisional application No. 60/074,218, Feb. 11, 1998.

[51] Int. Cl.$^7$ .......................... A01N 43/54; C07D 487/04
[52] U.S. Cl. ............................................ 514/258; 544/263
[58] Field of Search .................................... 544/263, 262; 514/258

[56] References Cited

U.S. PATENT DOCUMENTS

| | | | |
|---|---|---|---|
| 2,443,136 | 6/1948 | Heimbach et al. | 544/263 |
| 4,567,263 | 1/1986 | Eicken et al. | 544/263 |
| 4,863,843 | 9/1989 | Okushima et al. | 430/566 |
| 5,593,996 | 1/1997 | Pees et al. | 544/263 |

FOREIGN PATENT DOCUMENTS

| | | |
|---|---|---|
| 0 550 113 | 12/1992 | Germany . |
| 1-235957 | 9/1989 | Japan . |

OTHER PUBLICATIONS

Makisumi et al. Chem. Pharm. Bulletin, vol. 9 pp., 801–808, 1961.
G. Fisher, Advances in Heterocyclic Chemistry, vol. 57, 1993, pp. 81–138.

Primary Examiner—Mukund J. Shah
Assistant Examiner—V Balasubramanian
Attorney, Agent, or Firm—Timothy J. Babcock

[57] ABSTRACT

The novel compounds of formula I:

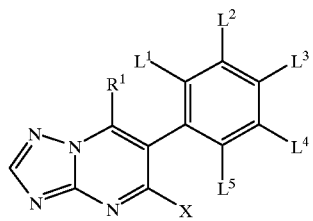

(I)

wherein $R^1$ represents an optionally substituted alkyl, alkenyl, alkynyl, alkadienyl, or aryl group, or an optionally substituted cycloalkyl or cycloalkenyl group, in which one $CH_2$ group may also be replaced by O, S or $NR^2$, in which $R^2$ represents a hydrogen atom or an alkyl group;

X represents a hydrogen or halogen atom, or an alkoxy, aryloxy, aralkyloxy, haloalkoxy, alkylthio, cyano, amino, alkylamino or dialkylamino group;

$L^1$, $L^2$, $L^3$, $L^4$ and $L^5$ each independently represent an hydrogen or halogen atom or an optionally substituted alkyl or alkoxy group or a nitro or cyano group show selective fungicidal activity. The new compounds are processed with carriers and, optionally, adjuvants, to afford fungicidal compositions, useful in agricultural applications.

20 Claims, No Drawings

FUNGICIDAL 7-ALKYL-TRIAZOLOPYRIMIDINES

This application claims priority from copending provisional application(s) Ser. No. 60/074,218 filed on Feb. 11, 1998.

BACKGROUND OF THE INVENTION

This invention relates to certain triazolopyrimidine compounds, a process for their preparation, compositions containing such compounds, a method for combating a fungus at a locus comprising treating the locus with such compounds and their use as fungicides.

EP-A-0 071 792 discloses compounds of the general formula

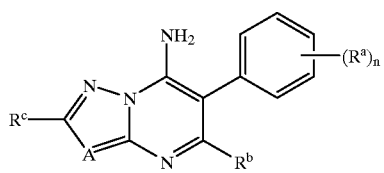

in which $R^b$ represents alkyl, halogen, alkoxy, cyano, cycloalkyl, aryl, aryloxy, arylthio, aralkyl, arylalkyl, arylalkyloxy or arylalkylthio each optionally substituted by halogen or alkoxy; or $(R^a)_n$ represents a benzene, indane or tetrahydronaphthalene ring fused with the phenyl ring, aromatic moieties in the above groups being optionally substituted by alkyl, alkoxy, halogen or cyano; n is 1 or 2; $R^b$ and $R^c$ are each hydrogen, alkyl or aryl, A represents a nitrogen atom or a $CR^d$ group, and $R^d$ is as $R^b$ but can also be halogen, cyano or alkoxycarbonyl or, together with $R^b$, can form an alkylene chain containing up to two double bonds. The compounds are said to be active against various phytopathogenic fungi, especially those of the phycomycete class. However, evidence of fungicidal activity is only provided for these compounds against *Plasmopara viticola*, a member of the oomycete class of fungi.

U.S. Pat. No. 5,593,996 discloses compounds of the general formula

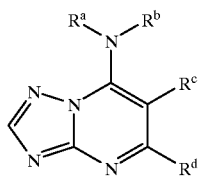

in which $R^a$ represents an optionally substituted alkyl, alkenyl, alkadienyl, cycloalkyl, bicycloalkyl or heterocyclyl group; $R^b$ represents a hydrogen atom or an alkyl group; or $R^a$ and $R^b$ together with the interjacent nitrogen atom represent an optionally substituted heterocyclic ring; $R^c$ represents an optionally substituted phenyl or naphthyl group; and $R^d$ represents a halogen atom or a group —$NR^eR^f$ where $R^e$ represents a hydrogen atom or an amino, alkyl, cycloalkyl or bicycloalkyl group and $R^f$ represents a hydrogen atom or an alkyl group.

Makisumi et al., Chem. Pharm Bull. 12 (2) 204–212, (1964) describe the preparation of 5,6,7-trimethyl-s-triazolo[1,5-a]pyrimidine. However, there is no disclosure of any fungicidal activity.

The broad generic formula of U.S. Pat. No. 4,863,843 suggests the use hydroxy-substituted triazolopyrimidines as components of photographic silver halide emulsions. However, there is no single 7-alkyl-6-aryl-5-hydroxytriazolopyrimidine disclosed. Moreover, there is no disclosure of fungicidal properties.

SUMMARY OF THE INVENTION

The present invention provides compounds of formula I

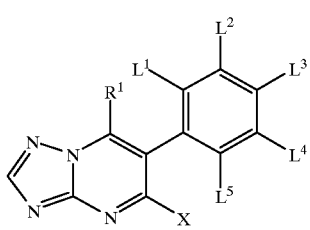

wherein
- $R^1$ represents an optionally substituted alkyl, alkenyl, alkynyl, alkadienyl, or aryl group, or an optionally substituted cycloalkyl or cycloalkenyl group, in which one $CH_2$ group may also be replaced by O, S or $NR^2$, in which $R^2$ represents a hydrogen atom or an alkyl group;
- X represents a hydrogen or halogen atom, or a hydroxy, alkoxy, aryloxy, aralkyloxy, haloalkoxy, alkylthio, cyano, amino, alkylamino or dialkylamino group;
- $L^1$, $L^2$, $L^3$, $L^4$ and $L^5$ each independently represent an hydrogen or halogen atom or an optionally substituted alkyl or alkoxy group or a nitro or cyano group.

These new compounds show an excellent selective fungicidal activity in various crops.

It is an object of the present invention to provide novel, selective fungicidal compounds.

It is a further object of the invention to provide methods for controlling an undesired fungus by contacting said plants with a fungicidally effective amount of the new compounds.

It is still another object of the invention to provide selective fungicidal compositions containing the new compounds as active ingredients.

These and other objects and features of the invention will be more apparent from the detailed description set forth hereinbelow, and from the appended claims.

DETAILED DESCRIPTION OF THE PREFERRED EMBODIMENTS

It has surprisingly been found that the compounds of formula I exhibit an excellent fungicidal activity against a broad range of fungi and thus have broad utility in the agricultural field.

In general terms, unless otherwise stated, as used herein the term "halogen atom" may denote a bromine, iodine, chlorine or fluorine atom, and is especially a bromine, chlorine or fluorine atom. Optionally substituted moieties may be unsubstituted or have from one up to the maximal possible number of substituents. Typically, 0 to 2 substituents are present.

In general terms, unless otherwise stated herein, the terms "alkyl," "alkenyl," "alkynyl," "alkadienyl" as used herein with respect to a radical or moiety refer to a straight or branched chain radical or moiety. As a rule, such radicals have up to 10, in particular up to 6 carbon atoms. Preferably an alkyl moiety has from 1 to 10 carbon atoms, preferably from 2 to 6 carbon atoms. A preferred alkyl moiety is an ethyl or especially a methyl, group. Preferably, an alkenyl moiety has from 2 to 6 carbon atoms.

In general terms, unless otherwise stated herein, the term "aryl," as used herein with respect to a radical or moiety refers to an aryl group having 6, 10 or 14 carbon atoms, preferably 6 or 10 carbon atoms, in particular, phenyl, being optionally substituted by one or more halogen atoms, nitro, cyano, alkyl, preferably $C_{1-6}$ alkyl, alkoxy, preferably $C_{1-6}$ alkoxy, haloalkyl, preferably $C_{1-6}$ haloalkyl, haloalkoxy, preferably $C_{1-6}$ haloalkoxy groups.

In general terms, unless otherwise stated herein, the terms "cycloalkyl" or "cycloalkenyl," as used herein with respect to a radical or moiety refer to a cycloalkyl group having 3 to 8 carbon atoms or a cycloalkenyl group having 5 to 8 carbon atoms, preferably 5 to 7 carbon atoms, in particular cyclopentyl, cyclohexyl or cyclohexenyl being optionally substituted by one or more halogen atoms, nitro, cyano, alkyl, preferably $C_{1-6}$ alkyl, alkoxy, preferably $C_{1-6}$ alkoxy.

In general terms, unless otherwise stated herein, the term "cycloalkyl or cycloalkenyl, in which one $CH_2$ group is replaced by O, S or $NR^2$," as used herein with respect to a radical or moiety, refers to a saturated or unsaturated heterocyclyl group having 5 or 6 ring atoms selected from carbon, oxygen, sulfur and nitrogen, one of which being oxygen, sulfur or nitrogen being optionally substituted by one or more halogen atoms, nitro, cyano, alkyl, preferably $C_{1-6}$ alkyl, alkoxy, preferably $C_{1-6}$ alkoxy, preferably 2,3-dehydropiperid-3-yl, tetrahydropyranyl, tetrahydrofuranyl or tetrahydrothienyl, in particular N-methyl-2,3-dehydropiperid-3-yl.

Preferred compounds of this are those compounds of the general formula I in which any alkyl part of the groups $R^1$, $R^2$ or X which may be straight chained or branched, contains 1 to 10 carbon atoms, preferably, 2 to 9 carbon atoms, more preferably, 3 to 6 carbon atoms, any alkenyl, alkynyl or alkadienyl part of the substituents $R^1$ contains 2 to 10 carbon atoms, preferably, 3 to 9 carbon atoms, more preferably, 4 to 6 carbon atoms, any cycloalkyl part of the substituents $R^1$ contains from 3 to 10 carbon atoms, preferably, from 3 to 8 carbon atoms, more preferably, from 3 to 6 carbon atoms, and any aryl part of the substituents $R^1$ contains 6, 10 or 14 carbon atoms, preferably, 6 or 10 carbon atoms, and in which each optionally substituted group independently is substituted by one or more halogen atoms or nitro, cyano, alkyl, preferably, $C_{1-6}$ alkyl, cycloalkyl, preferably, $C_{1-6}$ cycloalkyl, cycloalkenyl, preferably, $C_{3-6}$, cycloalkenyl, haloalkyl, preferably $C_{1-6}$ haloalkyl, halocycloalkyl, preferably $C_{3-6}$ halocycloalkyl, alkoxy, preferably $C_{1-6}$ alkoxy, alkanoyloxy, preferably $C_{1-6}$ alkanoyloxy, haloalkoxy, preferably $C_{1-6}$ haloalkoxy, alkylthio, preferably $C_{1-6}$ alkylthio, phenyl, halo-, dihalo- or trihalophenyl or pyridyl groups. Any alkyl, alkenyl or alkynyl group may be linear or branched. A halogen atom suitably denotes a fluorine, chlorine or iodine atom.

Especially preferred compound of this are compounds of the general formula I in which $R^1$ represents a $C_{1-10}$ alkyl, $C_{1-10}$ haloalkyl, in particular, a fluorinated $C_{1-10}$ alkyl group, $C_{3-6}$ cycloalkyl, $C_{3-8}$ cycloalkyl-$C_{1-6}$ alkyl, $C_{1-6}$ alkyl-$C_{3-8}$ cycloalkyl, in particular, a methylcyclohexyl group, halo-$C_{3-6}$ cycloalkyl, in particular a fluorocyclohexyl, most preferably a 3-or-4-fluorocyclohexyl group, $C_{5-8}$ cycloalkenyl, $C_{1-10}$ alkoxy-$C_{1-6}$alkyl, a phenyl, a mono- or di-$C_{1-6}$ alkyl-phenyl group, a phenyl-$C_{1-10}$ alkyl, or a mono- or di-$C_{1-6}$ alkyl-phenyl-$C_{1-10}$ alkyl group, in particular, a benzyl group.

Preferably at least one of the substituents $L^1$ through $L^5$, in particular $L^1$ and/or $L^5$, is different from hydrogen. $L^1$ is preferably a fluorine or chlorine atom or a methyl, methoxy or trifluoromethoxy group. The other substituents are preferably selected from hydrogen or fluorine.

Also, particularly preferred are compounds of formula 1, in which the phenyl group of formula

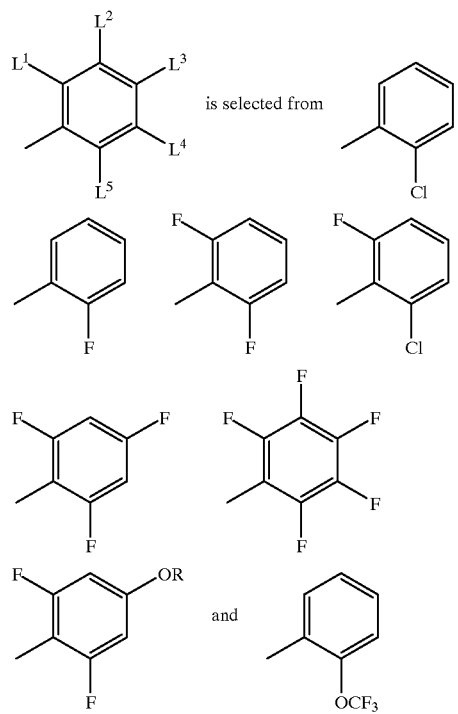

wherein R represents an alkyl group.

Most preferred are the 2-chloro-6-fluorophenyl, the 2,4,6-trifluorophenyl and the 2,6-difluoro-4-methoxyphenyl groups.

Also preferred are compounds of the general formula I in which X represents a halogen atom, in particular, a chlorine or iodine atom, a $C_{1-10}$ alkoxy, in particular, a methoxy or ethoxy group, a $C_{1-10}$ haloalkoxy, in particular a fluorinated $C_{1-10}$ alkoxy group, most preferably, a fluorinated methoxy or ethoxy group, a phenoxy, a mono- or di-$C_{1-6}$ alkylphenoxy group, a phenyl-$C_{1-10}$ alkoxy, or a mono- or di-$C_{1-6}$ alkylphenyl-$C_{1-10}$ alkoxy group, in particular, a benzyloxy group.

Included in the scope of the present invention are (R) and (S) isomers of compounds of general formula I having a chiral center and the racemates thereof, and salts, N-oxides and acid addition compounds.

The compounds according to general formula I are oils, gums, semi-solids or crystalline solid materials. They are superior by virtue of their valuable fungicidal properties, in particular, their fungitoxicity against a broad range of phytopathogenic fungi. For example, they can be used in agriculture or related fields for the control of phytopathogenic fungi such as *Alternaria solani, Botrytis cinerea, Cercospora beticola, Cladosporium herbarum, Corticium rolfsii, Erysiphe graminis, Helminthosporium tritici repentis, Leptosphaeria nodorum, Micronectriella nivalis, Monilinia fructigena, Mycosphaerella ligulicola, Mycosphaerella pinodes, Phytophthora infestans, Pyricularia grisea* f.sp. *oryzae, Rhizoctonia solani, Monographella nivalis Sclerotinia sclerotiorum, Uncinula necator* and *Venturia inaequalis*, in particular for the control of, *Alternaria solani Botrytis cinerea* and *Venturia inaequalis*. The compounds of general formula I according to the invention possess a high fungicidal activity within a wide concentration range and may be used in agriculture without any difficulties.

Moreover, the compounds according to the invention show enhanced residual control of fungi compared with conventional fungicides.

Good results in terms of control of phythopathogenic fungi are obtained with a compound as defined in formula I wherein:

X represents a halogen atom, an alkoxy or haloalkoxy group, in particular a chlorine or iodine atom or a methoxy, ethoxy, fluoromethoxy or 2,2,2-difluorethoxy group;

$R^1$ represents preferably straight chained or branched $C_1$–$C_8$-alkyl, in particular n-propyl, iso-propyl, 1- or 2-methylpropyl, n-butyl, n-pentyl or n-hexyl, $C_{3-7}$-cycloalkyl being optionally substituted by a fluorine atom, a $C_1$–$C_8$-alkyl group or a $C_2$–$C_8$-alkanoyloxy group, in particular cyclopentyl, cyclohexyl, 4-methylcyclohexyl, 4-acetoxycyclohexyl or 3- or 4-fluorocyclohexyl, straight chained or branched $C_1$–$C_6$-haloalkyl, in particular 3,3,3-trifluoropropyl, or phenyl being optionally substituted by at least one halogen atom or at least one $C_1$–$C_6$-alkyl or $C_1$–$C_6$-alkoxy group.

Particularly preferred are the compounds of formula IA,

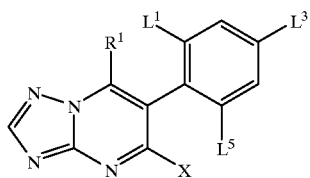

(IA)

wherein $R^1$ is as herein above defined, X represents a chlorine or iodine atom, or a methoxy or ethoxy group, and $L^1$, $L^2$ and $L^3$ each independently represent a hydrogen, fluorine or chlorine atom, or a methoxy, methyl, or trifluoromethoxy group, at least one of which is other than hydrogen.

Especially good results in terms of control of phytopathogenic fungi are obtained by using, for example, the following compounds of formula I:

5-chloro-6-phenyl-7-butyl-[1,2,4]triazolo[1,5-a]pyrimidine,
5-chloro-6-(2-chloro-6-fluorophenyl)-7-butyl-1,2,4triazolo[1,5-a]pyrimidine,
5-chloro-6-(2-chloro-6-fluorophenyl)-7-hexyl-1,2,4]triazolo[1,5-a]pyrimidine,
5-chloro-7-butyl-6-(2,4,6-trifluorophenyl)-[1,2,4]triazolo[1,5-a]pyrimidine,
5-chloro-7-butyl-6-(2-methylphenyl)-[1,2,4]triazolo[1,5-a]pyrimidine,
5-chloro-7-butyl-6-(2-chlorophenyl)-[1,2,4]triazolo[1,5-a]pyrimidine,
5-chloro-7-butyl-6-(2-fluorophenyl)-[1,2,4]triazolo[1,5-a]pyrimidine,
5-chloro-7-butyl-6-(2,6-difluorophenyl)-[1,2,4]triazolo[1,5-a]pyrimidine,
5-chloro-6-(2-chloro-6-fluorophenyl)-7-ethyl-1,2,4]triazolo[1,5-a]pyrimidine,
5-chloro-6-(2-chloro-6-fluorophenyl)-7-(2-methylpropyl[1,2,4]triazolo[1,5-a]pyrimidine, 5-chloro-6-(2-chloro-6-fluorophenyl)-7-(2-methylpropyl)-[1,2,4]triazolo[1,5-a]pyrimidine,
5-chloro-6-(2-chloro-6-fluorophenyl)-7-pentyl-[1,2,4]triazolo [1,5-a]pyrimidine,
5-chloro-6-(2-chloro-6-fluorophenyl)-7-isopropyl-[1,2,4]triazolo[1,5-a]pyrimidine,
5-chloro-6-(2-chloro-6-fluorophenyl)-7-(1-methylpropyl)-[1,2,4]triazolo[1,5-a]pyrimidine,
5-chloro-6-(2-chloro-6-fluorophenyl)-7-cyclopentyl-[1,2,4]triazolo[1,5-a]pyrimidine,
5-chloro-6-(2-chloro-6-fluorophenyl)-7-cyclohexyl-[1,2,4]triazolo[1,5-a]pyrimidine,
5-chloro-7-cyclohexyl-6-(2,4,6-trifluorophenyl)-[1,2,4]triazolo[1,5-a]pyrimidine,
7-cyclohexyl-5-methoxy-6-(2,4,6-trifluorophenyl)-[1,2,4]triazolo[1,5-a]pyrimidine,
7-cyclohexyl-6-(2,6-difluorophenyl)-5-methoxy-[1,2,4]triazolo[1,5-a]pyrimidine,
7-cyclohexyl-6-(2-fluorophenyl)-5-methoxy-[1,2,4]triazolo [1,5-a]pyrimidine,
6-(2-chloro-6-fluorophenyl)-7-cyclohexyl-5-methoxy-[1,2,4]triazolo[1,5-a]pyrimidine,
5-chloro-6-(2-chloro-6-fluorophenyl)-7-(4-methylcyclohexyl)-[1,2,4]triazolo[1,5-a]pyrimidine,
7-cyclohexyl-5-iodo-6-(2,4,6-trifluorophenyl)-[1,2,4]triazolo[1,5-a]pyrimidine,
5-chloro-7-cyclohexyl-6-(2,4-difluoro-6-methoxyphenyl)-[1,2,4]triazolo[1,5-a]pyrimidine,
7-(4-chloro-3-hydroxycyclohexyl)-5-chloro-6-(2,4,6-trifluorophenyl)-[1,2,4]triazolo[1,5-a]pyrimidine,
5-chloro-7-cyclohexyl-6-(2,6-difluoro-4-methoxyphenyl)-[1,2,4]triazolo[1,5-a]pyrimidine,
5-chloro-7-(cis-4-fluoro-3-cyclohexyl)-6-(2,4,6-trifluorophenyl)-[1,2,4]triazolo[1,5-a]pyrimidine,
5-chloro-7-(cis-3-fluoro-3-cyclohexyl)-6-(2,4,6-trifluorophenyl)-[1,2,4]triazolo[1,5-a]pyrimidine,
5-chloro-7-(trans-4-fluoro-3-cyclohexyl)-6-(2,4,6-trifluorophenyl)-[1,2,4]triazolo[1,5-a]pyrimidine,
7-cyclohexyl-5-(N-methylamino)-6-(2,4,6-trifluorophenyl)-[1,2,4]triazolo[1,5-a]pyrimidine,
7-cyclohexyl-5-(N,N-dimethylamino)-6-(2,4,6-trifluorophenyl)-[1,2,4]triazolo[1,5-a]pyrimidine,
5-chloro-7-cyclohex-3-enyl-6-(2,6-difluoro-4-methoxyphenyl)-[1,2,4]triazolo[1,5-a]pyrimidine,
7-(trans-4-fluoro-3-cyclohexyl)-5-methoxy-6-(2,4,6-trifluorophenyl)-[1,2,4]triazolo[1,5-a]pyrimidine,
7-cyclohexyl-6-(2,6-difluoro-4-methoxyphenyl)-5-ethoxy-[1,2,4]triazolo[1,5-a]pyrimidine,
7-cyclohexyl-6-(2,6-difluoro-4-methoxyphenyl)-5-isopropoxy-[1,2,4]triazolo[1,5-a]pyrimidine,
7-cyclohexyl-6-(2,6-difluoro-4-methoxyphenyl)-5-(2,2,2-trifluoroethoxy)-[1,2,4]triazolo[1,5-a]pyrimidine,
7-cyclohexyl-6-(2,6-difluoro-4-methoxyphenyl)-5-phenoxy-[1,2,4]triazolo[1,5-a]pyrimidine,
7-cyclohexyl-5-benzyloxy-6-(2,6-difluoro-4-methoxyphenyl)-[1,2,4]triazolo[1,5-a]pyrimidine,
5-chloro-7-(N-methyl-2,3-dehydropiperid-3-yl)-6-(2,4,6-trifluorophenyl)-[1,2,4]triazolo[1,5-a]pyrimidine,
5-chloro-6-(2,6-difluorophenyl)-7-(N-methyl-2,3-dehydropiperid-3-yl)-[1,2,4]triazolo[1,5-a]pyrimidine,
5-chloro-6-(2,6-difluoro-4-methoxyphenyl)-7-(N-methyl-2,3-dehydropiperid-3-yl)-[1,2,4]triazolo[1,5-a]pyrimidine,
5-chloro-6-(2-chloro-6-fluorophenyl)-7-(N-methyl-2,3-dehydropiperid-3-yl)-[1,2,4]triazolo[1,5-a]pyrimidine,
7-(4-acetoxycyclohexyl)-5-chloro-6-(2,4,6-trifluorophenyl)-[1,2,4]triazolo[1,5-a]pyrimidine,
7-(4-acetoxycyclohexyl)-5-chloro-6-(2,6-difluoro-4-methoxyphenyl)-[1,2,4]triazolo[1,5-a]pyrimidine,
5-chloro-6-(2,6-difluoro-4-methoxyphenyl)-7-(cis-4-fluorocyclohexyl)-[1,2,4]triazolo[1,5-a]pyrimidine,
5-chloro-6-(2,6-difluoro-4-methoxyphenyl)-7-(trans-4-fluorocyclohexyl)-[1,2,4]triazolo[1,5-a]pyrimidine,
5-chloro-6-(2,6-difluoro-4-methoxyphenyl)-7-(cis-3-fluorocyclohexyl)-[1,2,4]triazolo[1,5-a]pyrimidine,
6-(2,6-difluoro-4-methoxyphenyl)-7-(cis-4-fluorocyclohexyl)-5-methoxy-[1,2,4]triazolo[1,5-a]pyrimidine,
6-(2,6-difluoro-4-methoxyphenyl)-7-(trans-4-fluorocyclohexyl)-5-methoxy-[1,2,4]triazolo[1,5-a]pyrimidine, 6-(2,6-difluoro-4-methoxyphenyl)-7-(cis-3-fluorocyclohexyl)-5-methoxy-[1,2,4]triazolo[1,5-a]pyrimidine, 7-cyclohexyl-5-fluoromethoxy-6-(2,4,6-trifluorophenyl)-[1,2,4]triazolo[1,5-a]pyrimidine.

The present invention further provides a process for the preparation of a compound of formula I which comprises (a) reacting a 5,7-dihalo-triazolopyrimidine of formula II,

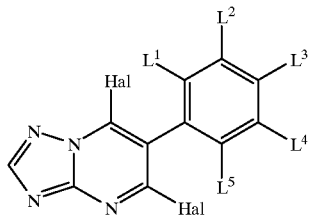

wherein $L^1$, $L^2$, $L^3$, $L^4$ and $L^5$ are as herinbefore defined for formula I and Hal represents a halogen atom, with a compound of formula III $$R^1\text{—Met} \quad (III)$$

wherein $R^1$ is hereinbefore defined for formula I,

Met represents a free or complexed metal atom, such as, for example, Li,

Mg or Zn in the presence of a transition metal, in particular, Cu, to afford a compound of formula I, in which X represents a halogen atom, and (b) optionally treating the resulting 5-halogentriazolopyrimidine with an alcohol or a thio-alcohol in the presence of a base, or with a metal amide, a metal alkylamide or a metal dialkylamide, or a metal cyanide.

The reaction between the 5,7-dihalo-6-phenyl-triazolopyrimidines of formula II, which are known from U.S. Pat. No. 5,593,996, and the compound of formula III is conveniently carried out in the presence of a solvent. Suitable solvents include ethers, such as dioxane, diethyl ether and, especially, tetrahydrofuran, hydrocarbons such as hexane, cyclohexane or mineral oil, and aromatic hydrocarbons, for example toluene, or mixtures of these solvents. The reaction is suitably carried out at a temperature in the range from about −100° C. to about +100° C., the preferred reaction temperature being from about −80° C. to about +40° C. It is also preferred that the reaction is carried out in the presence of copper ions, preferably equimolar amounts of copper(I) halides, in particular copper(I) iodide.

Furthermore, the compounds of formula I may be prepared by reacting the corresponding alkyl 2-aryl-3-alkyl-3-oxopropionates of formula IV

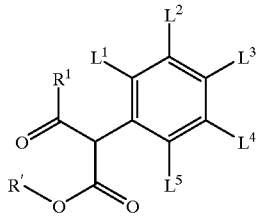

wherein $R^1$ and $L^1$, $L^2$, $L^3$, $L^4$, and $L^5$ are as hereinbefore defined for formula I and R' represents an optionally substituted alkyl group, with 2-amino-[1,3,4]-triazole.

This reaction is preferably carried out either at elevated temperatures in the presence of a tertiary amine, in particular tri-n-butylamine, analogously to the methods disclosed in EP 0 770 615, or in the presence of acetic acid analogously to the methods disclosed by G. Fischer in Advances in Heterocyclic Chemistry, Vol. 57, 1993, pages 81–138.

The resulting 7-substituted 5-hydroxytriazolopyrimidine of formula I, wherein X represents a hydroxy group, is subsequently treated with a halogenating agent, preferably selected from the group consisting of phosphorous oxychloride, phosphorous oxybromide, phosphorous pentachloride, phosphorous pentabromide, analogously to the methods disclosed in EP 0 770 615.

The compounds of formula 1, wherein $R^1$ represents a fluorocycloalkyl group, can be prepared by reaction of the corresponding compounds of formula I, wherein $R^1$ represents a cycloalkenyl group, with a fluorination agent, in particular with hydrogenfluoride. The reaction between the 7cycloalkenyl-triazolopyrimidines of formula I, and hydrogenfluoride is conveniently carried out in the presence of a tertiary amine. Suitable tertiary amines include pyridine, triethylamine, tri-n-butylamine or mixtures of these amines. The reaction is suitably carried out at a temperature in the range from about −20° C. to about +80° C., the preferred reaction temperature being from about 0° C. to about +40° C., and most preferably at ambient temperature.

The compounds of general formula I have been found to possess fungicidal activity. Accordingly, the invention further provides a fungicidal composition which comprises as the active ingredient at least one compound of formula I as defined above, and one or more carriers. A method of making such a composition is also provided which comprises bringing a compound of formula I as defined above into association with the carrier(s). Such a composition may contain a single active ingredient or a mixture of several active ingredients of the present invention. It is also envisaged that different isomers or mixtures of isomers may have different levels or spectra of activity and thus compositions may comprise individual isomers or mixtures of isomers.

A composition according to the invention preferably contains from 0.5% to 95% by weight (w/w) of active ingredient.

A carrier in a composition according to the invention is any material with which the active ingredient is formulated to facilitate application to the locus to be treated, which may be, for example, a plant, seed or soil, or to facilitate storage, transport or handling. A carrier may be a solid or a liquid, including material which is normally a gas but which has been compressed to form a liquid.

The compositions may be manufactured into a variety of formulations sutiable for agricultural use, e.g. emulsion concentrates, solutions, oil in water emulsions, wettable powders, soluble powders, suspension concentrates, dusts, granules, water dispersible granules, micro-capsules, gels and other formulation types by well-established procedures. These procedures include intensive mixing and/or milling of the active ingredients with other substances, such as fillers, solvents, solid carriers, surface active compounds (surfactants), and optionally solid and/or liquid auxilaries and/or adjuvants. The form of application such as spraying, atomizing, dispersing or pouring may be chosen like the compositions according to the desired objectives and the given circumstances.

Solvents may be aromatic hydrocarbons, e.g. Solvesso® 200, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. ethanol, ethyleneglycol mono- and dimethyl ether, ketones such as cyclohexanone, strongly polar solvents such as N-methyl-2-pyrrolidone, or γ-butyrolactone, higher alkyl pyrrolidones, e.g. n-octylpyrrolidone or cyclohexylpyrrolidone, epoxidized plant oil esters, e.g. methylated coconut or soybean oil ester and water. Mixtures of different liquids are often suitable solvents.

Solid carriers, which may be used for dusts, wettable powders, water dispersible granules, or granules, may be mineral fillers, such as calcite, talc, kaolin, montmorillonite or attapulgite. The physical properties may be improved by addition of highly dispersed silica gel or polymers. Carriers for granules may be porous material, e.g. pumice, kaolin, sepiolite, bentonite; non-sorptive carriers may be calcite or sand. Additionally, a multitude of pre-granulated inorganic or organic materials may be used, such as dolomite or crushed plant residues.

Pesticidal compositions are often formulated and transported in a concentrated form which is subsequently diluted by the user before application. The presence of small amounts of a carrier which is a surfactant facilitates this process of dilution. Thus, preferably at least one carrier in a composition according to the invention is a surfactant. For example, the composition may contain at two or more carriers, at least one of which is a surfactant.

Surfactants may be nonionic, anionic, cationic or zwitterionic substances with good dispersing, emulsifying and wetting properties depending on the nature of the compound according to general formula I to be formulated. Surfactants may also mean mixtures of individual surfactants.

The compositions of the invention may for example be formulated as wettable powders, water dispersible granules, dusts, granules, solutions, emulsifiable concentrates, emulsions, suspension concentrates and aerosols. Wettable powders usually contain 5 to 90% w/w of active ingredient and usually contain in addition to solid inert carrier, 3 to 10% w/w of dispersing and wetting agents and, where necessary, 0 to 10% w/w of stabilizer(s) and/or other additives such as penetrants or stickers. Dusts are usually formulated as a dust concentrate having a similar composition to that of a wettable powder but without a dispersant, and may be diluted in the field with further solid carrier to give a composition usually containing 0.5 to 10% w/w of active ingredient. Water dispersible granules and granules are usually prepared to have a size between 0.15 mm and 2.0 mm and may be manufactured by a variety of techniques. Generally, these types of granules will contain 0.5 to 90% w/w active ingredient and 0 to 20% w/w of additives such as stabilizer, surfactants, slow release modifiers and binding agents. The so-called "dry flowables" consist of relatively small granules having a relatively high concentration of active ingredient. Emulsifiable concentrates usually contain, in addition to a solvent or a mixture of solvents, 1 to 80% w/v active ingredient, 2 to 20% w/v emulsifiers and 0 to 20% w/v of other additives, such as stabilizers, penetrants and corrosion inhibitors. Suspension concentrates are usually milled so as to obtain a stable, non-sedimenting flowable product and usually contain 5 to 75% w/v active ingredient, 0.5 to 15% w/v of dispersing agents, 0.1 to 10% w/v of suspending agents such as protective colloids and thixotropic agents, 0 to 10% w/v of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation and crystalization or as antifreeze agents for water.

Aqueous dispersions and emulsions, for example, compositions obtained by diluting the formulated product according to the invention with water, also lie within the scope of the invention.

Of particular interest in enhancing the duration of the protective activity of the compounds of this invention is the use of a carrier which will provide slow release of the pesticidal compounds into the environment of a plant which is to be protected.

The biological activity of the active ingredient can also be increased by including an adjuvant in the spray dilution. An adjuvant is defined here as a substance which can increase the biological activity of an active ingredient but is not itself significantly biologically active. The adjuvant can either be included in the formulation as a coformulant or carrier, or can be added to the spray tank together with the formulation containing the active ingredient.

As a commodity the compositions of the present invention are preferably in a concentrated form which is then diluted for use by the end user. The concentrated compositions are typically diluted to a concentration down to 0.001% of active ingredient for applicaiton to the target. The typical doses usually are in the range from 0.01 to 10 kg a.i./ha.

Examples of formulations according to the invention are:

| Emulsion Concentrate (EC) | | |
|---|---|---|
| Active Ingredient | Compound of Example 44 | 30% (w/v) |
| Emulsifier(s) | Atlox ® 4856 B and Atlox ® 4857 B [1] | 5% (w/v) |
| Solvent | Shellsol ® A [2] | to 1000 ml |
| Suspension Concentrate (SC) | | |
| Active Ingredient | Compound of Example 44 | 50% (w/v) |
| Dispersing agent | Soprophor ® FL [3] | 3% (w/v) |
| Antifoaming agent | Rhodorsil ® 422 [3] | 0.2% (w/v) |
| Structure agent | Kelzan ® S [4] | 0.2% (w/v) |
| Antifreezing agent | Propylene glycol | 5% (w/v) |
| Biocidal agent | Proxel ® [5] | 0.1% (w/v) |
| Water | | to 1000 ml |
| Wettable Powder (WP) | | |
| Active Ingredient | Compound of Example 44 | 60% (w/w) |
| Wetting agent | Atlox ® 4995 [1] | 2% (w/w) |
| Dispersing agent | Witcosperse ® D-60 [6] | 3% (w/w) |
| Carrier/Filler | Kaolin | 35% (w/w) |
| Water Dispersible Granules | | |
| Active Ingredient | Compound of Example 44 | 50% (w/w) |
| Dispersing agent | Witcosperse ® D-450 [6] | 8% (w/w) |
| Wetting agent | Morwet ® EFW [6] | 2% (w/w) |
| Antifoaming agent | Rhodorsil ® EP 6703 [3] | 1% (w/w) |
| Disintegrant | Agrimer ® ATF [7] | 2% (w/w) |
| Carrier/Filler | Kaolin | 35% (w/w) |

[1] Product commercially available from ICI Surfactants
[2] Product commercially available from Deutsche Shell AG
[3] Product commercially available from Rhone-Poulenc
[4] Product commercially available from Kelco Co.
[5] Product commercially available from Zeneca
[6] Product commercially available from Witco
[7] Product commercially available from International Speciality Products The compositions of this invention can be applied to the plants or their environment simultaneous with, or in succession with, other active substances. These other active substances can be either fertilizers, agents which donate trace elements, or other preparations which influence plant growth. However, they can also be selective herbicides, insecticides, fungicides, bactericides, nematicides, algicides, molluscicides, rodenticides, virucides, compounds inducing resistance into plants, biological control agents such as viruses, bacteria, nematodes, fungi and other microorganisms, repellents of birds and animals, and plant growth regulators, or mixtures of several of these preparations, if appropriate together with other carrier substances conventionally used in the art of formulation, surfactants or other additives which promote application.

The compositions of this invention can comprise also other compounds having biological activity, e.g. compounds having similar or complementary fungicidal activity or compounds having plant growth regulating, herbicidal or insecticidal activity. Other fungicidal compounds can be, for example, those which are capable of combating diseases of cereals (e.g. wheat) such as those caused by Erysipha, Puccinia, Septoria, Gibberella and Helminthosporium spp., seed and soil borne diseases and downy and powdery mildews on vines and powdery mildew and scab on apples etc. These mixtures of fungicides can have a broader spectrum of activity than the compound of general formula I alone.

Examples of other fungicidal compounds which can be utilized in combination with the compounds of formula I are AC 382042, anilazine, azoxystrobin, benalaxyl, benomyl, binapacryl, bitertanol, blasticidin S, Bordeaux mixture, bromuconazole, bupirimate, captafol, captan, carbendazim, carboxin, carpropamid, chlorbenzthiazon, chlorothalonil, chlozolinate, copper-containing compounds such as copper oxychloride, and copper sulfate, cycloheximide, cymoxanil, cypofuram, cyproconazole, cyprodinil, dichlofluanid, dichlone, dichloran, diclobutrazol, diclocymet, diclomezine, diethofencarb, difenoconazole, diflumetorim, dimethirimol, dimethomorph, diniconazole, dinocap, ditalimfos, dithianon, dodemorph, dodine, edifenphos, epoxiconazole, etaconazole, ethirimol, etridiazole, famoxadone, fenapanil, fenamidone, fenarimol, fenbuconazole, fenfuram, fenhexamid, fenpiclonil, fenpropidin, fenpropimorph, fentin, fentin acetate, fentin hydroxide, ferimzone, fluazinam, fludioxonil, flumetover, fluquinconazole, flusilazole, flusulfamide, flutolanil, flutriafol, folpet, fosetyl-aluminium, fuberidazole, furalaxyl, furametpyr, guazatine, hexaconazole, IKF-916, imazalil, iminoctadine, ipconazole, iprodione, isoprothiolane, iprovalicarb, kasugamycin, KH-7281, kitazin P, kresoxim-methyl, mancozeb, maneb, mepanipyrim, mepronil, metalaxyl, metconazole, methfuroxam, MON 65500, myclobutanil, neoasozin, nickel dimethyldithiocarbamate, nitrothalisopropyl, nuarimol, ofurace, organo mercury compounds, oxadixyl, oxycarboxin, penconazole, pencycuron, phenazineoxide, phthalide, polyoxin D, polyram, probenazole, prochloraz, procymidione, propamocarb, propiconazole, propineb, pyrazophos, pyrifenox, pyrimethanil, pyroquilon, pyroxyfur, quinomethionate, quinoxyfen, quintozene, spiroxamine, SSF-126, SSF-129, streptomycin, sulfur, tebuconazole, tecloftalame, tecnazene, tetraconazole, thiabendazole, thifluzamide, thiophanate-methyl, thiram, tolclofosmethyl, tolylfluanid, triadimefon, triadimenol, triazbutil, triazoxide, tricyclazole, tridemorph, trifloxystrobin, triflumizole, triforine, triticonazole, validamycin A, vinclozolin, XRD-563, zarilamid, zineb, and ziram.

In addition, the co-formulations according to the invention may contain at least one compound of formula I and any of the following classes of biological control agents such as viruses, bacteria, nematodes, fungi, and other microorganism which are suitable to control insects, weeds or plant diseases or to induce host resistance in the plants. Examples of such biological control agents are: *Bacillus thuringiensis, Verticillium lecanii, Autographica californica* NPV, *Beauvaria bassiana, Ampelomyces quisqualis, Bacilis subtilis, Pseudomonas fluorescens, Steptomyces griseoviridis* and *Trichoderma harzianum.*

Moreover, the co-formulations according to the invention may contain at least one compound of formula I and a chemical agent that induces the systemic acquired resistance in plants such as, for example, isonicotinic acid or derivatives thereof, 2,2-dichloro-3,3-dimethylcyclopropylcarboxylic acid or BION.

The compounds of general formula I can be mixed with soil, peat or other rooting media for the protection of the plants against seed-borne, soil-borne or foliar fungal diseases.

The invention further provides the use as a fungicide of a compound of the general formula I as defined above or a composition as defined above, and a method for combating fungus at a locus, which comprises treating the locus, which may be, for example, plants subject to or subjected to fungal attack, seeds of such plants or the medium in which such plants are growing or are to be grown, with such a compound or composition.

The present invention is of wide applicability in the protection of crop and ornamental plants against fungal attack. Typical crops which may be protected include vines, grain crops such as wheat and barley, rice, sugar beet, top fruit, peanuts, potatoes and tomatoes. The duration of the protection is normally dependent on the individual compound selected, and also a variety of external factors, such as climate, whose impact is normally mitigated by the use of a suitable formulation.

The following examples further illustrate the present invention. It should be understood, however, that these examples should not serve to limit the scope of invention.

EXAMPLE 1

Preparation of 5-chloro-7-n-hexyl-6-(2-chloro-6-fluorophenyl)-1,2,4-triazolo[1,5a]pyrimidine Copper iodide (0.96 g, 5 mmol) is suspended in tetrohydrofuran (THF, 25 ml) under an inert gas atmosphere. The suspension is cooled to about −70° C. and n-hexyllithium (5 ml, 2M in hexanes) is added by syringe. The mixture is stirred for 45 minutes and 5,7-dichloro-6-(2-chloro-6-fluorophenyl)-1,2,4-triazolo[1,5a]pyrimidine (1.6 g, 5 mmol, obtained according to EP 0 770 615) is added as a solution in THF (10 ml). The reaction mixture is stirred for 15 minutes at about −70° C. The reaction mixture is then quenched with a mixture of aqueous saturated ammonium chloride/concentrated ammonia (9:1). The two phase mixture is separated. A brown oil is isolated from the organic layer which is subjected to a chromatographic purification (light petroleum, 20% to 40% ethylacetate), which yields the product as a crystalline residue (0.75 g, m.p. 55–57° C.).

EXAMPLE 2

2A Preparation of ethyl 2-(2-chloro-6-fluorophenyl)-3-(4-methylcyclohexyl)-3-oxopropionate Lithium diisopropylamide (0.18 mol) in tetrahydrofuran (270 ml) is added to a mixture of ethyl (2-chloro-6-fluorophenyl)acetate (38.1 g, 0.175 mol) and THF (200 ml) at −70° C. The reaction mixture is stirred for 2 hours at about −70° C. 4-Methylcyclohexanecarboxylic acid chloride (28.25 g, 0.175 mol) is added and the reaction mixture is allowed to warm up to room temperature over night. The reaction mixture is then quenched with hydrochloric acid (5N, 60 ml) and most of the organic solvent is distilled off under reduced pressure. From the remainder the product is extracted with light petroleum (200 ml). The organic layer is separated, washed with water, dried with magnesium sulphate and concentrated in vacuo to yield a yellow oil (63.5 g). This is filtered through silica (light petroleum, 3% ethyl acetate) to yield a pale yellow oil (27.2 g). The product is used in the next step without further purification.

2B Preparation of 5-hydroxy-7-(4-methylcyclohexyl)-6-(2-chloro-6-fluorophenyl )-1,2,4-triazolo[1,5a]pyrimidine A mixture of 2A (3.41 g, 10 mmol), aminotriazole (0.84 g, 10 mmol) and tributylamine (1.85 g) is heated to 160° C. for 2.5 hours. The reaction mixture is cooled and dissolved in water. The mixture is acidified with hydrochloric acid and extracted with ethyl acetate. Drying and evaporation of the organic phase yields a solid which is treated with light petroleum. 1.66 g of a tan powder is obtained (m.p. 235–240° C.).

2C Preparation of 5-chloro-7-(4-methylcyclohexyl)-6-(2-chloro-6-fluorophenyl)-1,2,4-triazolo[1,5a]pyrimidine A mixture of 2B (1.0 g, 2.77 mmol) and phosphorus oxychloride (2 ml) is heated to 110° C. for 3 hours. After cooling the mixture is dissolved in methylene chloride and water is added. The two phase mixture is stirred vigorously for 1 hr. The organic layer is separated, dried and evaporated in vacuo to yield a foam (0.8 g). Upon treatment with diisopropyl ether a tan powder (0.5 g) is obtained which melts at 190–194° C.

EXAMPLE 3

Preparation of 5-methoxy-7-cyclohexyl-6-(2-chloro-6-fluorophenyl)-1,2,4-triazolo[1,5a]pyrimidine A mixture of 5-chloro-7-cyclohexyl-6-(2-chloro-6-fluorophenyl)-1,2,4-triazolo[1,5a]pyrimidine (1.15 g, 3.2 mmol), sodium methylate (0.074 g, 3.2 mmol) and methanol (50 ml) is stirred at ambient temperature for 5.5 hours. The mixture is then poured into water and the product is extracted with methylene chloride. Drying and evaporating the solvent yields a crystalline residue which is treated with a mixture of diisopropylether/light petroleum. 0.85 g of colourless crystals are obtained melting at 193–196° C.

By similar procedures other nucleophilic groups such as azide, cyanide, fluorine, alkylamino, alkylthio, etc. can be introduced.

EXAMPLE 4

Preparation of 5-chloro-7-hydroxymethyl-6-(2-chloro-6-fluorophenyl)-1,2,4-triazolo[1,5a]pyrimidine A mixture of 5,7-dichloro-6-(2-chloro-6-fluorophenyl)-1,2,4-triazolo[1,5a]pyrimidine (1.9 g, 6 mmol), dibenzoylperoxide (1.04 g, 3 mmol ) and molecular sieves 3 A in methanol 50 ml are heated to reflux over night. The mixture is filtered and the sieves are washed thoroughly with ethyl acetate. The combined organic phases are washed with aqueous sodium carbonate, dried and concentrated in vacuo. Upon standing the product starts to crystallize. It is filtered off and washed with toluene and dried in vacuo. Yield: 1.07 g, F.p.: 172–173° C.

The hydroxy group can be derivatized by standard chemistry, e.g. chlorination, alkylation, acetylation etc. to furnish the derivatives listed in the table.

EXAMPLE 5

Preparation of 5-chloro-7-(4-fluorocyclohexyl)-6-(2,4,6-trifluorophenyl)-1,2,4-triazolo[1,5a]pyrimidine A mixture of 5-chloro-7-(4-cyclohex-3-enyl)-6-(2,4,6-trifluorophenyl)-1,2,4-triazolo[1,5a]pyrimidine (1.3 g, 3.5 mmol) and hydrogenfluoride in pyridine (70%, 8 ml) is stirred at ambient temperature for 2 hours. The mixture is then poured onto a mixture of ice/sodium hydrogencarbonate. The product is extracted from this mixture with ethyl acetate. Drying of the organic phase with magnesium sulfate and evaporation yields 1.4 g of a colourless oil. This is purified by flash chromatograpy giving rise to two product fractions: A, 0.35 g a colourless solid (m.p.: 153° C.) which is a mixture (1:2) of the trans 4-F and the trans 3-F products and B, 0.82 g a colourless solid (m.p.: 162–166° C.) being a mixture (6:1) of the 4-cis-F and 3 trans-F products as indicated by NMR analysis.

EXAMPLE 6

Preparation of 5-chloro-7-(N-methyl-2,3-dehydropiperid-3-yl)-6-(2,4,6-trifluorophenyl)-1,2,4-triazolo[1,5a]pyrimidine To a solution of 5,7-dichloro-6-(2,4,6-trifluorophenyl)-1,2,4-triazolo[1,5a]pyrimidine (1.0 g, 3.1 mmol) in methylene chloride (10 ml) is added N-methyl-2,3-dehydropiperidine (10 mmol) and triethylamine (0.5 ml). The mixture is stirred over night. The reaction mixture is extracted with aqueous IN hydrogen chloride, water and brine. It is dried and evaporated in vacuo. The crude product is purified by flash chromatography using light petroleum/ethyl acetate (1:1) as the eluent. Evaporation of the product containing fractions gives 0.55 g of bright orange crystals melting at 175° C.

EXAMPLE 7

Synthesis of 5-methoxy-6-aryl-7-alkyl-1,2,4-triazolo[1,5a]pyrimidines

7A Preparation of 5-chloro-7-cyclohexyl-6-(2,6-difluorophenyl)-1,2,4-triazolo[1,5a]pyri-midine To a solution of zinc bromide (8.1 g, 36 mmol) in 50 ml dry THF is added cyclohexylmagnesium chloride (2M in ether, 18 ml, 36 mmol). The milky white suspension is stirred at ambient temperature for 1 h. In a separate flask lithium chloride (3.05 g, 72 mmol) is dried at about 130° C. at 0.1 mbar for 1 h. CuCN (3.22 g, 36 mmol) is added and the flask is purged with argon. THF (36 ml) is added and the clear pale green solution is transferred to the previously prepared suspension of the cyclohexylzinc, cooled to −10° C., by syringe. The mixture is stirred at 0° C. for 10'. It is then cooled to −25° C. and 5,7-dichloro-6-(2,6-difluorophenyl)-1,2,4-triazolo[1,5a]pyrimidine (9.05 g, 30 mmol) is added as a solution in 30 ml THF. The mixture is allowed to warm to ambient temperature. Stirring is continued over night. The reaction mixture is then quenched with 100 ml of a mixture of aq. saturated ammonium chloride/conc. ammonia (9:1) and the two phase mixture is separated. The aqueous phase is extracted with dichloromethane. The organic phases are combined, dried and concentrated in vacuo. The resulting residue is treated with light petroleum. The tan crystals are recrystalized from isopropanol to yield colorless crystals, 7.11 g, m.p. 180–84° C.

7B Preparation of 5-methoxy-7-cyclohexyl-6-(2,6-difluorophenyl)-1,2,4-triazolo[1,5a]pyrimidine To a solution of 7A (0.25 g, 0.7 mmol) in 10 ml dry methanol is added methanolic sodium methoxide (1.4 ml, 0.7 mmol). The reaction mixture is stirred at ambient temperature for 1 hour. It is then quenched with water and the product is extracted with dichloromethane. Drying and evaporating the organic phases yields a colorless crystalline residue (0.22 g, 92%, m.p. 190–196° C.) which does not require further purification.

EXAMPLES 8–100

Using the synthetic procedures described in Examples 1 to 7, the following compounds are prepared and their structure and melting point are given in Table 1 below.

TABLE I

| Example | R¹ | L¹ | L³ | L⁵ | X | melting point (° C.) |
|---|---|---|---|---|---|---|
| 8 | methyl | F | H | Cl | Cl | 154–158 |
| 9 | hydroxymethyl | F | H | Cl | Cl | 180–184 |
| 10 | tetrahydrothien-2-yl | F | H | Cl | Cl | oil |
| 11 | tetrahydrofuran-2-yl | F | H | Cl | Cl | 118–121 |
| 12 | chloromethyl | F | H | Cl | Cl | 156–160 |
| 13 | acetoxymethyl | F | H | Cl | Cl | 107–108 |
| 14 | methoxymethyl | F | H | Cl | Cl | 176–180 |
| 15 | ethoxymethyl | F | H | Cl | Cl | 97–101 |
| 16 | tetrahydrofuran-2-yl | OCF₃ | H | H | Cl | 125 |
| 17 | n-butyl | F | H | Cl | Cl | 99–102 |
| 18 | n-pentyl | F | H | Cl | Cl | oil |
| 19 | n-butyl | CH₃ | H | H | Cl | 91–95 |
| 20 | n-butyl | Cl | H | H | Cl | 89–91 |
| 21 | n-butyl | F | H | H | Cl | 58–62 |
| 22 | n-butyl | F | H | F | Cl | 104–108 |
| 23 | n-butyl | H | H | H | Cl | 93–96 |
| 24 | ethyl | F | H | Cl | Cl | 150–154 |
| 25 | n-propyl | F | H | Cl | Cl | 72–75 |
| 26 | 2-methylpropyl | F | H | Cl | Cl | 122–125 |
| 27 | isopropyl | F | H | Cl | Cl | 179–183 |
| 28 | 1-methylpropyl | F | H | Cl | Cl | 142–145 |
| 29 | cyclopentyl | F | H | Cl | Cl | 189–195 |
| 30 | cyclohexyl | F | H | Cl | Cl | 186–190 |
| 31 | phenyl | F | H | Cl | Cl | 180–186 |
| 32 | 3,3,3-trifluoropropyl | F | H | Cl | Cl | 111–112 |
| 33 | 2,6-dimethylphenyl | F | H | Cl | Cl | 172–178 |
| 34 | 3-methylphenyl | F | H | Cl | Cl | 156–163 |
| 35 | 2-methylphenyl | F | H | Cl | Cl | 165–169 |
| 36 | 2,6-dioxocyclohexyl | F | H | Cl | Cl | 192–193 |
| 37 | cyclohexyl | F | H | Cl | F | 158 |
| 38 | cyclohexyl | F | H | Cl | OCH₃ | 190 |
| 39 | cyclohexyl | F | H | Cl | CN | 224–229 |
| 40 | cyclohexyl | F | H | F | Cl | 181–185 |
| 41 | 4-fluorophenyl | F | H | Cl | Cl | 169–174 |
| 42 | cyclohexyl | F | H | H | Cl | 176–179 |
| 43 | cyclohexyl | Cl | H | H | Cl | 217–221 |
| 44 | cyclohexyl | F | F | F | Cl | 135–140 |
| 45 | cyclohexyl | F | H | Cl | N₃ | 173–176 |
| 46 | cyclohexyl | F | H | Cl | SCH₃ | 229–233 |
| 47 | cyclohexyl | F | H | Cl | Br | 191–195 |
| 48 | cyclohexyl | F | H | Cl | NH₂ | 276–281 |
| 49 | cyclohexyl | F | F | F | OCH₃ | 193–197 |
| 50 | cyclohexyl | F | H | H | OCH₃ | 185–190 |
| 51 | cyclohex-3-enyl | F | H | Cl | Cl | 185 |
| 52 | 2-hydroxycyclohexyl | F | H | Cl | OCH₃ | |
| 53 | cyclohexyl | F | F | F | OC₂H₅ | 184.5–190 |
| 54 | cyclohexyl | F | H | Cl | OC₂H₅ | |
| 55 | cyclohexyl | F | F | F | OCH(CH₃)₂ | 197–201 |
| 56 | tetrahydrofuran-2-yl | F | F | F | Cl | |
| 57 | 2-fluorophenyl | F | F | F | Cl | 171 |
| 58 | 2-trifluoromethylphenyl | F | F | F | Cl | 202 |
| 59 | 2-fluorophenyl | F | F | F | Cl | 167 |
| 60 | 2,4,6-trifluorophenyl | F | F | F | Cl | 175 |
| 61 | 4-tert-butylphenyl | F | F | F | Cl | 169 |
| 62 | 2-hydroxycyclohexyl | Cl | H | F | OCH(CH₃)₂ | 182 |
| 63 | 3-fluorophenyl | F | F | F | Cl | 209 |
| 64 | cyclohexyl | F | F | F | F | 145 |
| 65 | cyclohexyl | F | F | F | I | 187 |
| 66 | cyclohexyl | OCH₃ | F | F | Cl | 170 |
| 67 | 3-hydroxy-4-chloro- | F | F | F | Cl | 205 |

TABLE I-continued

| Example | R¹ | L¹ | L³ | L⁵ | X | melting point (° C.) |
|---|---|---|---|---|---|---|
| | cyclohexyl | | | | | |
| 68 | cyclohexyl | F | OCH₃ | F | Cl | 189 |
| 69 | cyclohexyl | F | OCH₃ | F | OCH₃ | 168 |
| 70 | mixture of trans-3- and 4-fluorocyclohexyl | F | F | F | Cl | 153 |
| 71 | cis-4-fluorocyclohexyl | F | F | F | Cl | 162–166 |
| 72 | cyclohexyl | F | F | F | NHCH₃ | 290–293.5 |
| 73 | cyclohexyl | F | F | F | N(CH₃)₂ | 217–221 |
| 74 | cyclohex-3-enyl | F | OCH₃ | F | Cl | 194 |
| 75 | cis-4-fluorocyclohexyl | F | F | F | OCH₃ | 203–206 |
| 76 | cyclohexyl | F | OCH₃ | F | OC₂H₅ | 146 |
| 77 | cyclohexyl | F | OCH₃ | F | OCH(CH₃)₂ | 127 |
| 78 | cyclohexyl | F | OCH₃ | F | OCH₂CF₃ | 138 |
| 79 | cyclohexyl | F | OCH₃ | F | OC₆H₅ | 195 |
| 80 | cyclohexyl | F | OCH₃ | F | OCH₂C₆H₅ | 137 |
| 81 | N-methyl-2,3-dehydropiperid-3-yl | F | H | F | Cl | 195 |
| 82 | N-methyl-2,3-dehydrdpiperid-3-yl | F | OCH₃ | F | Cl | 170 |
| 83 | N-methyl-2,3-dehydropiperid-3-yl | F | H | Cl | Cl | 165 |
| 84 | 4-acetoxycyclohexyl | F | F | F | Cl | 70 |
| 85 | 4-acetoxycyclohexyl | F | OCH₃ | F | Cl | 90 |
| 86 | mixture of trans-3- and 4-fluorocyclohexyl | F | OCH₃ | F | Cl | 188 |
| 87 | cis-4-fluorocyclohexyl | F | OCH₃ | F | Cl | 201 |
| 88 | mixture of trans-3- and 4-fluorocyclohexyl | F | OCH₃ | F | OCH₃ | 157 |
| 89 | cis-4-fluorocyclohexyl | F | OCH₃ | F | OCH₃ | 181 |
| 90 | cyclohexyl | F | F | F | OCH₂F | 185 |
| 91 | 3-methylpro-3-enyl | F | OCH₃ | F | Cl | 66–68 |
| 92 | 3-methylpro-3-enyl | F | OCH₃ | F | OCH₃ | 91–92 |
| 93 | propyl | F | OCH₃ | F | Cl | 72–77 |
| 94 | 2-methylpropyl | F | OCH₃ | F | Cl | 100–105 |
| 95 | tetrahydrofuran-2-yl | F | OCH₃ | F | Cl | semi-solid |
| 96 | butyl | F | OCH₃ | F | Cl | semi-solid |
| 97 | cyclopentyl | F | OCH₃ | F | Cl | semi-solid |
| 98 | propyl | F | OCH₃ | F | OCH₃ | semi-solid |
| 99 | cyclopentyl | F | OCH₃ | F | OCH₃ | semi-solid |
| 100 | 2-methylpropyl | F | OCH₃ | F | OCH₃ | semi-solid |

EXAMPLES 101 and 102

5-chloro-7-cyclohexyl-6-(pentafluorophenyl)-1,2,4-triazolo[1,5a]pyrimidine (101)(melting point: 188–193° C.) and 5-chloro-7-(4-methylcyclohexyl)-6-(pentaflurophenyl)-1,2,4-triazolo[1,5a]pyrimidine (102) are obtained analogously to examples 7A and 2, respectively.

Biological Investigations

Determination of Minimum Inhibitory Concentration by Test Compounds in the Serial Dilution Test with Various Phytopathogenic Fungi The MIC (Minimum Inhibitory Concentration) value, which indicates the lowest concentration of the active ingredient in the growth medium which causes a total inhibition of myecelial growth, is determined by serial dilution tests using Microtiter plates with 24 or 48 wells per plate. The dilution of the test compounds in the nutrient solution and the distribution to the wells is carried out by a TECAN RSP 5000 Robotic Sample Processor. The following test compound concentrations are used: 0.05, 0.10, 0.20, 0.39, 0.78, 1.56, 3.13, 6.25, 12.50, 25.00, 50.00 and 100.00 μg/ml. For preparation of the nutrient solution, V8 vegetable juice (333 ml) is mixed with calcium carbonate (4.95 g), centrifuged, the supernatant (200 ml) diluted with water (800 ml) and autoclaved at 121° C. for 30 min. The respective inocula (*Alternaria solani*, ALTESO; *Botrytis cinerea*, BOTRCI; *Leptosphaeria nodorum*, LEPTNO; *Phytophthora infestans*, PHYTIN; *Magnaporthe grisea* f. sp. oryzae, PYRIOR; *Pyrenophora teres*, PYRNTE; *Rhizoctonia solani*, RHIZSO; *Sclerotinia sclerotiorum*, SCLESC; *Mycosphaerella ligulicola*, MYCOLG; *Monilina fructigena*, MONIFG) are added into the wells as spore suspensions (50 μl; 5×10⁵/ml) or agar slices (6 mm) of an agar culture of the fungus. After 6–12 days incubation at suitable temperatures (18–25° C.), the MIC values are determined by visual inspection of the plates (Tables II and III; 0=not tested).

TABLE II
| Example | ALTESO | BOTRCI | LEPTNO | PHYTIN | PYRIOR | PYRNTE | RHIZSO |
|---|---|---|---|---|---|---|---|
| 1 | 0 | 0 | 12.5 | 100 | 1.56 | 3.13 | 0 |
| 2 | 0.1 | 0.2 | 0 | >100 | <0.05 | 1.56 | >100 |
| 6 | 3.13 | 25 | 25 | >100 | 0.78 | 0 | >100 |
| 7 | 1.56 | 12.5 | >100 | >100 | 1.56 | >100 | >100 |
| 19 | 1.56 | 12.5 | 12.5 | 50 | 0.78 | 6.25 | >100 |
| 20 | 0.2 | 1.56 | 3.13 | >100 | <0.05 | 3.13 | 3.13 |
| 21 | 0.1 | 1.56 | 3.13 | 100 | <0.05 | 0.78 | 3.13 |
| 22 | 0.1 | 1.56 | 1.56 | >100 | 0.1 | 6.25 | 1.56 |
| 23 | 6.25 | >100 | >100 | 50 | 25 | >100 | >100 |
| 24 | 12.5 | 6.25 | 3.13 | >100 | <0.05 | >100 | 6.25 |
| 25 | 1.56 | 0.78 | >100 | 12.5 | 0.1 | 3.13 | 1.56 |
| 26 | 0.78 | 0.2 | 0.39 | >100 | <0.05 | 3.13 | 0.78 |
| 27 | >100 | 0.78 | 1.56 | >100 | 0.2 | >100 | 0.39 |
| 28 | 6.25 | 3.13 | >100 | >100 | 1.56 | 6.25 | 0.78 |
| 29 | 0.78 | 1.56 | 0.39 | >100 | <0.05 | 0.78 | 0.78 |
| 30 | <0.05 | <0.05 | 25 | >100 | <0.05 | 0.2 | >100 |
| 32 | 3.13 | 0.78 | >100 | 50 | 0.2 | 12.5 | 6.25 |
| 33 | >100 | >100 | >100 | 6.25 | 12.5 | >100 | >100 |
| 34 | 1.56 | 6.25 | 25 | 50 | 0.78 | >100 | >100 |
| 35 | 3.13 | 3.13 | 6.25 | 25 | 0.78 | >100 | 3.13 |
| 36 | >100 | >100 | >100 | 12.5 | >100 | >100 | >100 |
| 37 | 0.78 | 0.39 | >100 | >100 | 3.13 | >100 | >100 |
| 37 | 0.2 | 1.56 | >100 | >100 | 0.39 | >100 | >100 |
| 38 | 100 | >100 | >100 | >100 | 0.78 | >100 | >100 |
| 40 | 0.1 | 0.39 | >100 | >100 | 0.39 | 3.13 | >100 |
| 41 | 1.56 | 3.13 | >100 | >100 | 0.1 | 3.13 | 3.13 |
| 42 | 0.39 | 1.56 | 0.39 | >100 | 0.39 | 3.13 | >100 |
| 43 | 1.56 | >100 | 1.56 | >100 | 0.39 | >100 | >100 |
| 44 | <0.05 | <0.05 | 0.2 | >100 | <0.05 | 0.2 | 0.78 |
| 45 | 100 | >100 | >100 | >100 | 12.5 | >100 | >100 |
| 49 | 0.2 | 0 | >100 | >100 | 0.39 | 1.56 | >100 |
| 50 | >100 | >100 | >100 | >100 | 25 | >100 | >100 |
| 68 | <0.05 | <0.05 | 0.39 | >100 | <0.05 | 0 | 0.78 |
| 69 | <0.05 | <0.05 | 1.56 | >100 | <0.05 | 0 | 3.13 |
| 70 | <0.05 | 0.10 | 0.78 | >100 | <0.05 | 0 | 3.13 |
| 71 | <0.05 | 0.20 | 0.78 | >100 | <0.05 | 0 | 6.25 |
| 74 | <0.05 | <0.05 | 0.78 | >100 | <0.05 | 0 | 0.39 |
| 75 | 1.56 | 6.25 | 12.5 | >100 | 0.39 | 0 | >100 |
| 84 | 3.13 | 12.5 | 12.5 | >100 | 3.13 | 0 | 100 |
| 85 | 0.78 | 1.56 | 6.25 | 25 | 0.78 | 0 | >100 |
| 86 | <0.05 | 0.10 | 0.39 | >100 | <0.05 | 0 | >100 |
| 87 | <0.05 | <0.05 | 0.39 | >100 | <0.05 | 0 | >100 |
| 88 | <0.05 | 1.56 | 3.13 | >100 | <0.05 | 0 | >100 |
| 89 | <0.05 | 1.56 | 6.25 | >100 | <0.05 | 0 | 12.5 |
| 91 | <0.05 | 0.39 | 6.25 | 50 | 0.39 | 0 | 1.56 |
| 92 | <0.05 | 1.56 | >100 | >100 | <0.05 | 0 | 3.13 |
| 93 | 0.2 | 0.2 | 6.25 | 100 | <0.05 | 0 | 0.39 |
| 94 | 0.1 | 0.2 | 3.13 | >100 | <0.05 | 0 | 0.2 |
| 95 | 0.2 | 0.78 | 3.13 | 100 | 0.1 | 0 | 3.13 |
| 96 | <0.05 | 0.1 | 3.13 | >100 | <0.05 | 0 | 0.78 |
| 97 | <0.05 | 0.2 | 6.25 | >100 | 0.1 | 0 | 0.39 |
| 98 | 1.56 | 3.13 | 100 | >100 | 0.2 | 0 | 1.56 |
| 99 | 0.39 | 0.78 | >100 | >100 | 0.39 | 0 | 1.56 |
| 100 | 0.39 | 0.78 | >100 | >100 | <0.05 | 0 | 1.56 |
| 101 | 0.2 | 0.78 | 0.2 | >100 | 0.2 | 3.13 | >100 |
TABLE III
| Example | BOTRCI | LEPTNO | SCLESC | MYCOLG | MONIFG |
|---|---|---|---|---|---|
| 11 | 1.56 | 1.56 | 25 | 12.5 | 3.13 |
| 16 | 25 | >100 | >100 | >100 | >100 |
| 17 | 0.2 | 0.78 | 0.78 | 0.78 | 3.13 |
| 18 | 0.2 | 1.56 | 0.78 | 0.78 | 3.13 |
What is claimed is:
1. A compound of formula I
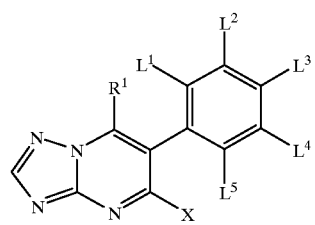
(I)

wherein
- R¹ represents an optionally substituted alkyl, alkenyl, alkynyl, alkadienyl, or aryl group, or an optionally substituted cycloalkyl or cycloalkenyl group, in which one $CH_2$ group may also be replaced by O, S or $NR^2$, in which $R^2$ represents a hydrogen atom or an alkyl group;
- X represents a hydrogen or halogen atom, or an alkoxy, aryloxy, aralkyloxy, haloalkoxy, alkylthio, cyano, alkylamino or dialkylamino group;
- $L^1$, $L^2$, $L^3$, $L^4$ and $L^5$ each independently represent a hydrogen or halogen atom or an optionally substituted alkyl or alkoxy group or a nitro or cyano group;
- in which each optionally substituted group independently may be substituted by one or more halogen atoms or nitro, cyano, alkyl, cycloalkyl, cycloalkenyl, haloalkyl, halocycloalkyl, alkoxy, alkanoyloxy, haloalkoxy, alkylthio, phenyl, halophenyl, dihalophenyl, trihalophenyl or pyridyl groups.

2. A compound according to claim 1 in which at least one of $L^1$ and $L^5$ represents a halogen atom.

3. A compound according to claim 1 in which $R^1$ represents an optionally substituted $C_{2-10}$ alkyl, $C_{3-8}$ cycloalkyl or phenyl group.

4. A compound according to claim 1 in which X represents a chlorine or iodine atom or a methoxy or ethoxy group.

5. A compound according to claim 1, wherein X represents a chlorine or iodine atom, or a methoxy or ethoxy group, and $L^1$, $L^3$ and $L^5$ each independently represent a hydrogen, fluorine or chlorine atom, or a methoxy, methyl, or trifluoromethoxy group, provided that at least one of $L^1$, $L^3$ and $L^5$ is different from hydrogen.

6. A compound according to claim 1 selected from the group consisting of:
- 5-chloro-6-phenyl-7-butyl-[1,2,4]triazolo[1,5-a]pyrimidine;
- 5-chloro-6-(2-chloro-6-fluorophenyl)-7-butyl-[1,2,4]triazolo[1,5-a]pyrimidine;
- 5-chloro-6-(2-chloro-6-fluorophenyl)-7-hexyl-[1,2,4]triazolo[1,5-a]pyrimidine;
- 5-chloro-7-butyl-6-(2,4,6-trifluorophenyl)-[1,2,4]triazolo[1,5-a]pyrimidine;
- 5-chloro-7-butyl-6-(2-methylphenyl)-[1,2,4]triazolo[1,5-a]pyrimidine;
- 5-chloro-7-butyl-6-(2-chlorophenyl)-[1,2,4]triazolo[1,5-a]pyrimidine;
- 5-chloro-7-butyl-6-(2-fluorophenyl)-[1,2,4]triazolo[1,5-a]pyrimidine;
- 5-chloro-7-butyl-6-(2,6-difluorophenyl)-[1,2,4]triazolo[1,5-a]pyrimidine;
- 5-chloro-6-(2-chloro-6-fluorophenyl)-7-ethyl-[1,2,4]triazolo[1,5-a]pyrimidine;
- 5-chloro-6-(2-chloro-6-fluorophenyl)-7-propyl-[1,2,4]triazolo[1,5-a]pyrimidine;
- 5-chloro-6-(2-chloro-6-fluorophenyl)-7-(2-methylpropyl)-[1,2,4]triazolo[1,5-a]pyrimidine;
- 5-chloro-6-(2-chloro-6-fluorophenyl)-7-pentyl-[1,2,4]triazolo[1,5-a]pyrimidine;
- 5-chloro-6-(2-chloro-6-fluorophenyl)-7-isopropyl-[1,2,4]triazolo[1,5-a]pyrimidine;
- 5-chloro-6-(2-chloro-6-fluorophenyl)-7-(1-methylpropyl)-[1,2,4]triazolo[1,5-a]pyrimidine;
- 5-chloro-6-(2-chloro-6-fluorophenyl)-7-cyclopentyl-[1,2,4]triazolo[1,5-a]pyrimidine;
- 5-chloro-6-(2-chloro-6-fluorophenyl)-7-cyclohexyl-[1,2,4]triazolo[1,5-a]pyrimidine;
- 5-chloro-7-cyclohexyl-6-(2,4,6-trifluorophenyl)-[1,2,4]triazolo[1,5-a]pyrimidine;
- 7-cyclohexyl-5-methoxy-6-(2,4,6-trifluorophenyl)-[1,2,4]triazolo[1,5-a]pyrimidine;
- 7-cyclohexyl-6-(2,6-difluorophenyl)-5-methoxy-[1,2,4]triazolo[1,5-a]pyrimidine;
- 7-cyclohexyl-6-(2-fluorophenyl)-5-methoxy-[1,2,4]triazolo[1,5-a]pyrimidine;
- 6-(2-chloro-6-fluorophenyl)-7-cyclohexyl-5-methoxy-[1,2,4]triazolo[1,5-a]pyrimidine;
- 5-chloro-6-(2-chloro-6-fluorophenyl)-7-(4-methylcyclohexyl)-[1,2,4]triazolo[1,5-a]pyrimidine;
- 7-cyclohexyl-5-iodo-6-(2,4,6-trifluorophenyl)-[1,2,4]triazolo[1,5-a]pyrimidine;
- 5-chloro-7-cyclohexyl-6-(2,4-difluoro-6-methoxyphenyl)-[1,2,4]triazolo[1,5-a]pyrimidine;
- 7-(4-chloro-3-hydroxycyclohexyl)-5-chloro-6-(2,4,6-trifluorophenyl)-[1,2,4]triazolo[1,5-a]pyrimidine;
- 5-chloro-7-cyclohexyl-6-(2,6-difluoro-4-methoxyphenyl)-[1,2,4]triazolo[1,5-a]pyrimidine;
- 5-chloro-7-(cis-4-fluoro-3-cyclohexyl)-6-(2,4,6-trifluorophenyl)-[1,2,4]triazolo[1,5-a]pyrimidine;
- 5-chloro-7-(cis-3-fluoro-3-cyclohexyl)-6-(2,4,6-trifluorophenyl)-[1,2,4]triazolo[1,5-a]pyrimidine;
- 5-chloro-7-(trans-4-fluoro-3-cyclohexyl)-6-(2,4,6-trifluorophenyl)-[1,2,4]triazolo[1,5-a]pyrimidine;
- 7-cyclohexyl-5-(N-methylamino)-6-(2,4,6-trifluorophenyl)-[1,2,4]triazolo[1,5-a]pyrimidine;
- 7-cyclohexyl-5-(N,N-dimethylamino)-6-(2,4,6-trifluorophenyl)-[1,2,4]triazolo[1,5-a]pyrimidine;
- 5-chloro-7-cyclohex-3-enyl-6-(2,6-difluoro-4-methoxyphenyl)-[1,2,4]triazolo[1,5-a]pyrimidine;
- 7-(trans-4-fluoro-3-cyclohexyl)-5-methoxy-6-(2,4,6-trifluorophenyl)-[1,2,4]triazolo[1,5-a]pyrimidine;
- 7-cyclohexyl-6-(2,6-difluoro-4-methoxyphenyl)-5-ethoxy-[1,2,4]triazolo[1,5-a]pyrimidine;
- 7-cyclohexyl-6-(2,6-difluoro-4-methoxyphenyl)-5-isopropoxy-[1,2,4]triazolo[1,5-a]pyrimidine;
- 7-cyclohexyl-6-(2,6-difluoro-4-methoxyphenyl)-5-(2,2,2-trifluoroethoxy)-[1,2,4]triazolo[1,5-a]pyrimidine;
- 7-cyclohexyl-6-(2,6-difluoro-4-methoxyphenyl)-5-phenoxy-[1,2,4]triazolo[1,5-a]pyrimidine;
- 7-cyclohexyl-5-benzyloxy-6-(2,6-difluoro-4-methoxyphenyl)-[1,2,4]triazolo[1,5-a]pyrimidine;
- 5-chloro-7-(N-methyl-2,3-dehydropiperid-3-yl)-6-(2,4,6-trifluorophenyl)-[1,2,4]triazolo[1,5-a]pyrimidine;
- 5-chloro-6-(2,6-difluorophenyl)-7-(N-methyl-2,3-dehydropiperid-3-yl)-[1,2,4]triazolo[1,5-a]pyrimidine;
- 5-chloro-6-(2,6-difluoro-4-methoxyphenyl)-7-(N-methyl-2,3-dehydropiperid-3-yl)-[1,2,4]triazolo[1,5-a]pyrimidine;
- 5-chloro-6-(2-chloro-6-fluorophenyl)-7-(N-methyl-2,3-dehydropiperid-3-yl)-[1,2,4]triazolo[1,5-a]pyrimidine;
- 7-(4-acetoxycyclohexyl)-5-chloro-6-(2,4,6-trifluorophenyl)-[1,2,4]triazolo[1,5-a]pyrimidine;
- 7-(4-acetoxycyclohexyl)-5-chloro-6-(2,6-difluoro-4-methoxyphenyl)-[1,2,4]triazolo[1,5-a]pyrimidine;
- 5-chloro-6-(2,6-difluoro-4-methoxyphenyl)-7-(cis-4-fluorocyclohexyl)-[1,2,4]triazolo[1,5-a]pyrimidine;
- 5-chloro-6-(2,6-difluoro-4-methoxyphenyl)-7-(trans-4-fluorocyclohexyl)-[1,2,4]triazolo[1,5-a]pyrimidine;
- 5-chloro-6-(2,6-difluoro-4-methoxyphenyl)-7-(cis-3-fluorocyclohexyl)-[1,2,4]triazolo[1,5-a]pyrimidine;
- 6-(2,6-difluoro-4-methoxyphenyl)-7-(cis-4-fluorocyclohexyl)-5-methoxy-[1,2,4]triazolo[1,5-a]pyrimidine;
- 6-(2,6-difluoro-4-methoxyphenyl)-7-(trans-4-fluorocyclohexyl)-5-methoxy-[1,2,4]triazolo[1,5-a]pyrimidine;

6-(2,6-difluoro-4-methoxyphenyl)-7-(cis-3-fluorocyclohexyl)-5-methoxy-[1,2,4]triazolo[1,5-a]pyrimidine; and 7-cyclohexyl-5-fluoromethoxy-6-(2,4,6-trifluorophenyl)-[1,2,4]triazolo[1,5-a]pyrimidine.

7. A process for the preparation of a compound of formula I

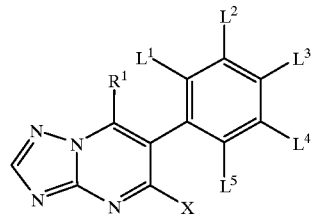

(I)

wherein
R¹ represents an optionally substituted alkyl, alkenyl, alkynyl, alkadienyl, or aryl group, or an optionally substituted cycloalkyl or cycloalkenyl group, in which one $CH_2$ group may also be replaced by O, S or $NR^2$, in which $R^2$ represents a hydrogen atom or an alkyl group;

X represents a hydrogen or halogen atom, or an alkoxy, aryloxy, aralkyloxy, haloalkoxy, alkylthio, cyano, alkylamino or dialkylamino group;

$L^1$, $L^2$, $L^3$, $L^4$ and $L^5$ each independently represent a hydrogen or halogen atom or an optionally substituted alkyl or alkoxy group or a nitro or cyano group;

in which each optionally substituted group independently may be substituted by one or more halogen atoms or nitro, cyano, alkyl, cycloalkyl, cycloalkenyl, haloalkyl, halocycloalkyl, alkoxy, alkanoyloxy, haloalkoxy, alkylthio, phenyl, halophenyl, dihalophenyl, trihalophenyl or pyridyl groups;

which process comprises
(a) treating a compound of formula II

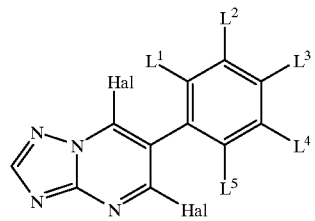

(II)

wherein
$L^1$, $L^2$, $L^3$, $L^4$ and $L^5$ are as hereinbefore defined and Hal represents a halogen atom;
with a compound of formula III R¹—Met (III)

in which
R¹ is as hereinbefore defined,
Met represents a metal atom,
in the presence of a transition metal to afford a compound of formula I, in which X represents a halogen atom, and
(b) optionally treating the resulting 5-halogentriazolopyrimidine with an alcohol, a thioalcohol in the presence of a base, or with a metal alkylamide or a metal dialkylamide or a metal cyanide.

8. A fungicidal composition which comprises a carrier, and as active agent, at least one compound of formula I

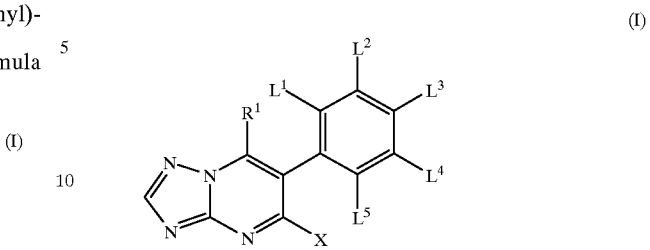

(I)

wherein
R¹ represents an optionally substituted alkyl, alkenyl, alkynyl, alkadienyl, or aryl group, or an optionally substituted cycloalkyl or cycloalkenyl group, in which one $CH_2$ group may also be replaced by O, S or $NR^2$, in which $R^2$ represents a hydrogen atom or an alkyl group;

X represents a hydrogen or halogen atom, or a hydroxy, alkoxy, aryloxy, aralkyloxy, haloalkoxy, alkylthio, cyano, alkylamino or dialkylamino group;

$L^1$, $L^2$, $L^3$, $L^4$ and $L^5$ each independently represent a hydrogen or halogen atom or an optionally substituted alkyl or alkoxy group or a nitro or cyano group;

in which each optionally substituted group independently may be substituted by one or more halogen atoms or nitro, cyano, alkyl, cycloalkyl, cycloalkenyl, haloalkyl, halocycloalkyl, alkoxy, alkanoyloxy, haloalkoxy, alkylthio, phenyl, halophenyl, dihalophenyl, trihalophenyl or pyridyl groups.

9. A composition according to claim 8 in which at least one of $L^1$ and $L^5$ represents a halogen atom.

10. A composition according to claim 8 in which R¹ represents an optionally substituted $C_{2-10}$ alkyl, $C_{3-8}$ cycloalkyl or phenyl group.

11. A composition according to claim 8 in which X represents a chlorine or iodine atom or a methoxy or ethoxy group.

12. A composition according to claim 8 wherein X represents a chlorine or iodine atom, or a methoxy or ethoxy group, and $L^1$, $L^3$ and $L^5$ each independently represent a hydrogen, fluorine or chlorine atom, or a methoxy, methyl, or trifluoromethoxy group, provided that at least one of $L^1$, $L^3$ and $L^5$ is different from hydrogen.

13. A composition according to claim 8 wherein the compound of formula I is selected from the group consisting of:

5-chloro-6-phenyl-7-butyl-[1,2,4]triazolo[1,5-a]pyrimidine;

5-chloro-6-(2-chloro-6-fluorophenyl)-7-butyl-[1,2,4]triazolo[1,5-a]pyrimidine;

5-chloro-6-(2-chloro-6-fluorophenyl)-7-hexyl-[1,2,4]triazolo[1,5-a]pyrimidine;

5-chloro-7-butyl-6-(2,4,6-trifluorophenyl)-[1,2,4]triazolo[1,5-a]pyrimidine;

5-chloro-7-butyl-6-(2-methylphenyl)-[1,2,4]triazolo[1,5-a]pyrimidine;

5-chloro-7-butyl-6-(2-chlorophenyl)-[1,2,4]triazolo[1,5-a]pyrimidine;

5-chloro-7-butyl-6-(2-fluorophenyl)-[1,2,4]triazolo[1,5-a]pyrimidine;

5-chloro-7-butyl-6-(2,6-difluorophenyl)-[1,2,4]triazolo[1,5-a]pyrimidine;

5-chloro-6-(2-chloro-6-fluorophenyl)-7-ethyl-[1,2,4]triazolo[1,5-a]pyrimidine;

5-chloro-6-(2-chloro-6-fluorophenyl)-7-propyl-[1,2,4]triazolo[1,5-a]pyrimidine;
5-chloro-6-(2-chloro-6-fluorophenyl)-7-(2-methylpropyl)-[1,2,4]triazolo[1,5-a]pyrimidine;
5-chloro-6-(2-chloro-6-fluorophenyl)-7-pentyl-[1,2,4]triazolo[1,5-a]pyrimidine;
5-chloro-6-(2-chloro-6-fluorophenyl)-7-isopropyl-[1,2,4]triazolo[1,5-a]pyrimidine;
5-chloro-6-(2-chloro-6-fluorophenyl)-7-(1-methylpropyl)-[1,2,4]triazolo[1,5-a]pyrimidine;
5-chloro-6-(2-chloro-6-fluorophenyl)-7-cyclopentyl-[1,2,4]triazolo[1,5-a]pyrimidine;
5-chloro-6-(2-chloro-6-fluorophenyl)-7-cyclohexyl-[1,2,4]triazolo[1,5-a]pyrimidine;
5-chloro-7-cyclohexyl-6-(2,4,6-trifluorophenyl)-[1,2,4]triazolo[1,5-a]pyrimidine;
7-cyclohexyl-5-methoxy-6-(2,4,6-trifluorophenyl)-[1,2,4]triazolo[1,5-a]pyrimidine;
7-cyclohexyl-6-(2,6-difluorophenyl)-5-methoxy-[1,2,4]triazolo[1,5-a]pyrimidine;
7-cyclohexyl-6-(2-fluorophenyl)-5-methoxy-[1,2,4]triazolo[1,5-a]pyrimidine;
6-(2-chloro-6-fluorophenyl)-7-cyclohexyl-5-methoxy-[1,2,4]triazolo[1,5-a]pyrimidine;
5-chloro-6-(2-chloro-6-fluorophenyl)-7-(4-methylcyclohexyl)-[1,2,4]triazolo[1,5-a]pyrimidine;
7-cyclohexyl-5-iodo-6-(2,4,6-trifluorophenyl)-[1,2,4]triazolo[1,5-a]pyrimidine;
5-chloro-7-cyclohexyl-6-(2,4-difluoro-6-methoxyphenyl)-[1,2,4]triazolo[1,5-a]pyrimidine;
7-(4-chloro-3-hydroxycyclohexyl)-5-chloro-6-(2,4,6-trifluorophenyl)-[1,2,4]triazolo[1,5-a]pyrimidine;
5-chloro-7-cyclohexyl-6-(2,6-difluoro-4-methoxyphenyl)-[1,2,4]triazolo[1,5-a]pyrimidine;
5-chloro-7-(cis-4-fluoro-3-cyclohexyl)-6-(2,4,6-trifluorophenyl)-[1,2,4]triazolo[1,5-a]pyrimidine;
5-chloro-7-(cis-3-fluoro-3-cyclohexyl)-6-(2,4,6-trifluorophenyl)-[1,2,4]triazolo[1,5-a]pyrimidine;
5-chloro-7-(trans-4-fluoro-3-cyclohexyl)-6-(2,4,6-trifluorophenyl)-[1,2,4]triazolo[1,5-a]pyrimidine;
7-cyclohexyl-5-(N-methylamino)-6-(2,4,6-trifluorophenyl)-[1,2,4]triazolo[1,5-a]pyrimidine;
7-cyclohexyl-5-(N,N-dimethylamino)-6-(2,4,6-trifluorophenyl)-[1,2,4]triazolo[1,5-a]pyrimidine;
5-chloro-7-cyclohex-3-enyl-6-(2,6-difluoro-4-methoxyphenyl)-[1,2,4]triazolo[1,5-a]pyrimidine;
7-(trans-4-fluoro-3-cyclohexyl)-5-methoxy-6-(2,4,6-trifluorophenyl)-[1,2,4]triazolo[1,5-a]pyrimidine;
7-cyclohexyl-6-(2,6-difluoro-4-methoxyphenyl)-5-ethoxy-[1,2,4]triazolo[1,5-a]pyrimidine;
7-cyclohexyl-6-(2,6-difluoro-4-methoxyphenyl)-5-isopropoxy-[1,2,4]triazolo[1,5-a]pyrimidine;
7-cyclohexyl-6-(2,6-difluoro-4-methoxyphenyl)-5-(2,2,2-trifluoroethoxy)-[1,2,4]triazolo[1,5-a]pyrimidine;
7-cyclohexyl-6-(2,6-difluoro-4-methoxyphenyl)-5-phenoxy-[1,2,4]triazolo[1,5-a]pyrimidine;
7-cyclohexyl-5-benzyloxy-6-(2,6-difluoro-4-methoxyphenyl)-[1,2,4]triazolo[1,5-a]pyrimidine;
5-chloro-7-(N-methyl-2,3-dehydropiperid-3-yl)-6-(2,4,6-trifluorophenyl)-[1,2,4]triazolo[1,5-a]pyrimidine;
5-chloro-6-(2,6-difluorophenyl)-7-(N-methyl-2,3-dehydropiperid-3-yl)-[1,2,4]triazolo[1,5-a]pyrimidine;
5-chloro-6-(2,6-difluoro-4-methoxyphenyl)-7-(N-methyl-2,3-dehydropiperid-3-yl)-[1,2,4]triazolo[1,5-a]pyrimidine;
5-chloro-6-(2-chloro-6-fluorophenyl)-7-(N-methyl-2,3-dehydropiperid-3-yl)-[1,2,4]triazolo[1,5-a]pyrimidine;
7-(4-acetoxycyclohexyl)-5-chloro-6-(2,4,6-trifluorophenyl)-[1,2,4]triazolo[1,5-a]pyrimidine;
7-(4-acetoxycyclohexyl)-5-chloro-6-(2,6-difluoro-4-methoxyphenyl)-[1,2,4]triazolo[1,5-a]pyrimidine;
5-chloro-6-(2,6-difluoro-4-methoxyphenyl)-7-(cis-4-fluorocyclohexyl)-[1,2,4]triazolo[1,5-a]pyrimidine;
5-chloro-6-(2,6-difluoro-4-methoxyphenyl)-7-(trans-4-fluorocyclohexyl)-[1,2,4]triazolo[1,5-a]pyrimidine;
5-chloro-6-(2,6-difluoro-4-methoxyphenyl)-7-(cis-3-fluorocyclohexyl)-[1,2,4]triazolo[1,5-a]pyrimidine;
6-(2,6-difluoro-4-methoxyphenyl)-7-(cis-4-fluorocyclohexyl)-5-methoxy-[1,2,4]triazolo[1,5-a]pyrimidine;
6-(2,6-difluoro-4-methoxyphenyl)-7-(trans-4-fluorocyclohexyl)-5-methoxy-[1,2,4]triazolo[1,5-a]pyrimidine;
6-(2,6-difluoro-4-methoxyphenyl)-7-(cis-3-fluorocyclohexyl)-5-methoxy-[1,2,4]triazolo[1,5-a]pyrimidine; and
7-cyclohexyl-5-fluoromethoxy-6-(2,4,6-trifluorophenyl)-[1,2,4]triazolo[1,5-a]pyrimidine.

14. A method of combating fungus at a locus which comprises treating the locus with a fungicidally effective amount of a compound of formula I

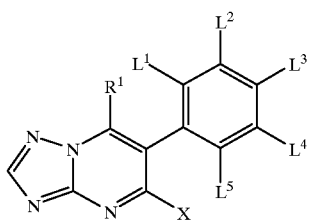

(I)

wherein
R$^1$ represents an optionally substituted alkyl, alkenyl, alkynyl, alkadienyl, or aryl group, or an optionally substituted cycloalkyl or cycloalkenyl group, in which one CH$_2$ group may also be replaced by O, S or NR$^2$, in which R$^2$ represents a hydrogen atom or an alkyl group;

X represents a hydrogen or halogen atom, or a hydroxy, alkoxy, aryloxy, aralkyloxy, haloalkoxy, alkylthio, cyano, alkylamino or dialkylamino group;

L$^1$, L$^2$, L$^3$, L$^4$ and L$^5$ each independently represent a hydrogen or halogen atom or an optionally substituted alkyl or alkoxy group or a nitro or cyano group;

in which each optionally substituted group independently may be substituted by one or more halogen atoms or nitro, cyano, alkyl, cycloalkyl, cycloalkenyl, haloalkyl, halocycloalkyl, alkoxy, alkanoyloxy, haloalkoxy, alkylthio, phenyl, halophenyl, dihalophenyl, trihalophenyl or pyridyl groups.

15. A method according to claim 14 in which at least one of L$^1$ and L$^5$ represents a halogen atom.

16. A method according to claim 14 in which R$^1$ represents an optionally substituted C$_{2-10}$ alkyl, C$_{3-8}$ cycloalkyl or phenyl group.

17. A method according to claim 14 in which X represents a chlorine or iodine atom or a methoxy or ethoxy group.

18. A method according to claim 14 wherein X represents a chlorine or iodine atom, or a methoxy or ethoxy group, and L$^1$, L$^3$ and L$^5$ each independently represent a hydrogen, fluorine or chlorine atom, or a methoxy, methyl, or trifluoromethoxy group, provided that at least one of L¹, L³ and L⁵ is different from hydrogen.

19. A method according to claim 14 wherein the compound of formula I is selected from the group consisting of:

5-chloro-6-phenyl-7-butyl-[1,2,4]triazolo[1,5-a]pyrimidine;
5-chloro-6-(2-chloro-6-fluorophenyl)-7-butyl-[1,2,4]triazolo[1,5-a]pyrimidine;
5-chloro-6-(2-chloro-6-fluorophenyl)-7-hexyl-[1,2,4]triazolo[1,5-a]pyrimidine;
5-chloro-7-butyl-6-(2,4,6-trifluorophenyl)-[1,2,4]triazolo[1,5-a]pyrimidine;
5-chloro-7-butyl-6-(2-methylphenyl)-[1,2,4]triazolo[1,5-a]pyrimidine;
5-chloro-7-butyl-6-(2-chlorophenyl)-[1,2,4]triazolo[1,5-a]pyrimidine;
5-chloro-7-butyl-6-(2-fluorophenyl)-[1,2,4]triazolo[1,5-a]pyrimidine;
5-chloro-7-butyl-6-(2,6-difluorophenyl)-[1,2,4]triazolo[1,5-a]pyrimidine;
5-chloro-6-(2-chloro-6-fluorophenyl)-7-ethyl-[1,2,4]triazolo[1,5-a]pyrimidine;
5-chloro-6-(2-chloro-6-fluorophenyl)-7-propyl-[1,2,4]triazolo[1,5-a]pyrimidine;
5-chloro-6-(2-chloro-6-fluorophenyl)-7-(2-methylpropyl)-[1,2,4]triazolo[1,5-a]pyrimidine;
5-chloro-6-(2-chloro-6-fluorophenyl)-7-pentyl-[1,2,4]triazolo[1,5-a]pyrimidine;
5-chloro-6-(2-chloro-6-fluorophenyl)-7-isopropyl-[1,2,4]triazolo[1,5-a]pyrimidine;
5-chloro-6-(2-chloro-6-fluorophenyl)-7-(1-methylpropyl)-[1,2,4]triazolo[1,5-a]pyrimidine;
5-chloro-6-(2-chloro-6-fluorophenyl)-7-cyclopentyl-[1,2,4]triazolo[1,5-a]pyrimidine;
5-chloro-6-(2-chloro-6-fluorophenyl)-7-cyclohexyl-[1,2,4]triazolo[1,5-a]pyrimidine;
5-chloro-7-cyclohexyl-6-(2,4,6-trifluorophenyl)-[1,2,4]triazolo[1,5-a]pyrimidine;
7-cyclohexyl-5-methoxy-6-(2,4,6-trifluorophenyl)-[1,2,4]triazolo[1,5-a]pyrimidine;
7-cyclohexyl-6-(2,6-difluorophenyl)-5-methoxy-[1,2,4]triazolo[1,5-a]pyrimidine;
7-cyclohexyl-6-(2-fluorophenyl)-5-methoxy-[1,2,4]triazolo[1,5-a]pyrimidine;
6-(2-chloro-6-fluorophenyl)-7-cyclohexyl-5-methoxy-[1,2,4]triazolo[1,5-a]pyrimidine;
5-chloro-6-(2-chloro-6-fluorophenyl)-7-(4-methylcyclohexyl)-[1,2,4]triazolo[1,5-a]pyrimidine;
7-cyclohexyl-5-iodo-6-(2,4,6-trifluorophenyl)-[1,2,4]triazolo[1,5-a]pyrimidine;
5-chloro-7-cyclohexyl-6-(2,4-difluoro-6-methoxyphenyl)-[1,2,4]triazolo[1,5-a]pyrimidine;
7-(4-chloro-3-hydroxycyclohexyl)-5-chloro-6-(2,4,6-trifluorophenyl)-[1,2,4]triazolo[1,5-a]pyrimidine;
5-chloro-7-cyclohexyl-6-(2,6-difluoro-4-methoxyphenyl)-[1,2,4]triazolo[1,5-a]pyrimidine;
5-chloro-7-(cis-4-fluoro-3-cyclohexyl)-6-(2,4,6-trifluorophenyl)-[1,2,4]triazolo[1,5-a]pyrimidine;
5-chloro-7-(cis-3-fluoro-3-cyclohexyl)-6-(2,4,6-trifluorophenyl)-[1,2,4]triazolo[1,5-a]pyrimidine;
5-chloro-7-(trans-4-fluoro-3-cyclohexyl)-6-(2,4,6-trifluorophenyl)-[1,2,4]triazolo[1,5-a]pyrimidine;
7-cyclohexyl-5-(N-methylamino)-6-(2,4,6-trifluorophenyl)-[1,2,4]triazolo[1,5-a]pyrimidine;
7-cyclohexyl-5-(N,N-dimethylamino)-6-(2,4,6-trifluorophenyl)-[1,2,4]triazolo[1,5-a]pyrimidine;
5-chloro-7-cyclohex-3-enyl-6-(2,6-difluoro-4-methoxyphenyl)-[1,2,4]triazolo[1,5-a]pyrimidine;
7-(trans-4-fluoro-3-cyclohexyl)-5-methoxy-6-(2,4,6-trifluorophenyl)-[1,2,4]triazolo[1,5-a]pyrimidine;
7-cyclohexyl-6-(2,6-difluoro-4-methoxyphenyl)-5-ethoxy-[1,2,4]triazolo[1,5-a]pyrimidine;
7-cyclohexyl-6-(2,6-difluoro-4-methoxyphenyl)-5-isopropoxy-[1,2,4]triazolo[1,5-a]pyrimidine;
7-cyclohexyl-6-(2,6-difluoro-4-methoxyphenyl)-5-(2,2,2-trifluoroethoxy)-[1,2,4]triazolo[1,5-a]pyrimidine;
7-cyclohexyl-6-(2,6-difluoro-4-methoxyphenyl)-5-phenoxy-[1,2,4]triazolo[1,5-a]pyrimidine;
7-cyclohexyl-5-benzyloxy-6-(2,6-difluoro-4-methoxyphenyl)-[1,2,4]triazolo[1,5-a]pyrimidine;
5-chloro-7-(N-methyl-2,3-dehydropiperid-3-yl)-6-(2,4,6-trifluorophenyl)-[1,2,4]triazolo[1,5-a]pyrimidine;
5-chloro-6-(2,6-difluorophenyl)-7-(N-methyl-2,3-dehydropiperid-3-yl)-[1,2,4]triazolo[1,5-a]pyrimidine;
5-chloro-6-(2,6-difluoro-4-methoxyphenyl)-7-(N-methyl-2,3-dehydropiperid-3-yl)-[1,2,4]triazolo[1,5-a]pyrimidine;
5-chloro-6-(2-chloro-6-fluorophenyl)-7-(N-methyl-2,3-dehydropiperid-3-yl)-[1,2,4]triazolo[1,5-a]pyrimidine;
7-(4-acetoxycyclohexyl)-5-chloro-6-(2,4,6-trifluorophenyl)-[1,2,4]triazolo[1,5-a]pyrimidine;
7-(4-acetoxycyclohexyl)-5-chloro-6-(2,6-difluoro-4-methoxyphenyl)-[1,2,4]triazolo[1,5-a]pyrimidine;
5-chloro-6-(2,6-difluoro-4-methoxyphenyl)-7-(cis-4-fluorocyclohexyl)-[1,2,4]triazolo[1,5-a]pyrimidine;
5-chloro-6-(2,6-difluoro-4-methoxyphenyl)-7-(trans-4-fluorocyclohexyl)-[1,2,4]triazolo[1,5-a]pyrimidine;
5-chloro-6-(2,6-difluoro-4-methoxyphenyl)-7-(cis-3-fluorocyclohexyl)-[1,2,4]triazolo[1,5-a]pyrimidine;
6-(2,6-difluoro-4-methoxyphenyl)-7-(cis-4-fluorocyclohexyl)-5-methoxy-[1,2,4]triazolo[1,5-a]pyrimidine;
6-(2,6-difluoro-4-methoxyphenyl)-7-(trans-4-fluorocyclohexyl)-5-methoxy-[1,2,4]triazolo[1,5-a]pyrimidine;
6-(2,6-difluoro-4-methoxyphenyl)-7-(cis-3-fluorocyclohexyl)-5-methoxy-[1,2,4]triazolo[1,5-a]pyrimidine; and
7-cyclohexyl-5-fluoromethoxy-6-(2,4,6-trifluorophenyl)-[1,2,4]triazolo[1,5-a]pyrimidine.

20. A method according to claim 14 wherein the locus is treated with the compound at a dosage rate of from 0.01 to 10 kg a.i./ha.

* * * * *